United States Patent
Seifart et al.

(10) Patent No.: US 6,576,758 B1
(45) Date of Patent: *Jun. 10, 2003

(54) NUCLEIC ACID CONSTRUCTS CONTAINING HYBRID PROMOTERS

(75) Inventors: Klaus-Heinrich Seifart, Marburg (DE); Rolf Mueller, Marburg (DE); Hans-Harald Sedlacek, Marburg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/936,603

(22) Filed: Sep. 24, 1997

(30) Foreign Application Priority Data

Sep. 24, 1996 (DE) .......................... 196 39 103

(51) Int. Cl.$^7$ .......................... C12N 15/63; C12N 15/11; C12N 15/62; C12N 15/67
(52) U.S. Cl. .................. 536/24.1; 435/320.1; 536/23.1
(58) Field of Search .............................. 435/320.1, 325; 514/44; 536/23.1, 23.4, 23.5, 24.1

(56) References Cited

U.S. PATENT DOCUMENTS

| | | | |
|---|---|---|---|
| 5,654,168 A | * 8/1997 | Bujard et al. | |
| 5,830,880 A | 11/1998 | Sedlacek et al. | ............... 514/44 |
| 5,854,019 A | 12/1998 | Sedlacek et al. | ........... 435/69.1 |
| 5,885,833 A | 3/1999 | Mueller et al. | ............. 435/372 |
| 5,916,803 A | 6/1999 | Sedlacek et al. | ......... 435/320.1 |
| 5,965,440 A | * 10/1999 | Reeves | |
| 6,033,856 A | * 3/2000 | Koerner et al. | |

FOREIGN PATENT DOCUMENTS

| | | |
|---|---|---|
| EP | 0 464 633 B1 | 1/1994 |
| WO | WO 95/21927 | 8/1995 |
| WO | WO 96/05994 | 2/1996 |
| WO | WO 96/06938 | 3/1996 |
| WO | WO 96/06940 | 3/1996 |
| WO | WO 96/06941 | 3/1996 |
| WO | WO 96/06943 | 3/1996 |
| WO | WO 97/44447 | 11/1997 |

OTHER PUBLICATIONS

Robinson et al (1995) Human Gene Therapy 6:137–143).*
Meissner W et al.: "Development of an inducible pol III transcription system essentially requiring a mutated form of the TAT–binding protein." Nucleic Acids Research 2001, vol. 29, No. 8, Apr. 15, 2001, 1672–82, Oxford University Press, Oxford, England, UK.
H.H. Sedlacek et al., "Contributions to Oncology" 32, *Monoclonal Antibodies in Tumor Therapy,* pp. 48–80, (1988).
H.H. Sedlacek et al., "Contributions to Oncology" 43, *Antibodies as Carriers of Cytotixicity,* pp. 114–133, (1992).
Tooze (ed), "DNA Tumor Viruses", *The SV40 Nucleotide Sequence,* pp. 799–841.

Shaw, A. et al., "The Ick Tyrosine Protein Kinase Interacts with the Cytoplasmic Tail of the CD4 Glycoprotein through Its Unique Amino–Terminal Domain", *Cell,* vol. 59, pp. 627–636 (1989).
Guddat, U. et al., "Protein–Mediated Nuclear Export of RNA: 5S rRNA Containing Small RNPs in Xenopus Oocytes", *Cell,* vol. 60, pp. 619–628 (1990).
Ahmad, M. et al., "Cell type–specific Transactivation of the VCAM–1 Promoter through an NF–κB Enhancer Motif", *The Journal of Biol. Chem.,* vol. 270, pp. 8976–8983 (1995).
Aird, et al., "Human von Willebrand factor gene sequences target expression to a subpopulation of endothelial cells in transgenic mice", *Proc. Natl. Acad. Sci. USA,* vol. 92, pp. 4567–4571 (1995).
Albert, M.J. et al., "Cultivation and Characterization of Human Rotaviruses with "Super Short" RNA Patterns", *Journal of Clinical Microbiology,* vol. 25, No. 1, pp. 183–185 (1987).
Alberti, S. et al., "C1q Binding and Activation of the Complement Classical Pathway by Klebsiella pneumoniae Outer Membrane Proteins", *Infection and Immunity,* vol. 61, No. 3, pp. 852–860 (1993).
Anderson, S.K. et al., "Human Cellular src Gene: Nucleotide Sequence and Derived Amino Acid Sequence of the Region Coding for the Carboxy–Terminal Two–Thirds of pp60$^{c-src}$" *Molecular and Cellular Biology,* vol. 5, No. 5, pp. 1122–1129 (1985).
Anderson, E.L. et al., "Evaluation of Rhesus Rotavirus Vaccine (MMU 18006) in Infants and Young Children", *The Journal of Infectious Diseases,* vol. 153, No. 5, pp. 823–831 (1986).
Arnon, R. et al., "Structural basis of antigenic specificity and design of new vaccines", *The FASEB, Journal,* vol. 6, pp. 3265–3274 (1992).
Augustin–Voss, et al., "Migrating Endothelial Cells Are Distinctly Hyperglycosylated and Express Specific Migration–associated Cell Surfaces Glycoproteins", *The Journal of Cell Biology,* vol. 119, No. 2, pp. 483–491 (1992).

(List continued on next page.)

Primary Examiner—Remy Yucel
Assistant Examiner—Bronwen M. Loeb
(74) Attorney, Agent, or Firm—Heller Ehrman White and McAuliffe

(57) ABSTRACT

Nucleic acid constructs containing hybrid promoters for use in gene therapy and genetic manipulation. The invention relates to a nucleic acid construct for the precise, regulated expression of genes in host cells, which construct exhibits at least one mutation which inhibits the proper expression of the expressed gene and exhibits at least one additional second mutation which relieves the inhibition due to the first mutation, to an isolated cell which harbors the nucleic acid construct, and to the use of the nucleic acid construct for preparing pharmaceuticals and for treating diseases with excessive cell proliferation.

17 Claims, 6 Drawing Sheets

OTHER PUBLICATIONS

Auron, P.E., et al., "Nucleotide sequence of human monocyte interleukin 1 precursor cDNA", *Proc. Natl. Acad. Sci. USA,* vol. 81, pp. 7907–7911 (1984).

Austin, E.A., et al., "A First Step in the Development of Gene Therapy for Colorectal Carcinoma: Cloning, Sequencing, and Expression of *Escherichia coli* Cytosine Deaminase", *Molecular Pharmacology,* vol. 43, pp. 380–387 (1993).

Bartley, T.D., et al., "B61 is a ligand for the ECK receptor protein–tyrosine kinase", *Nature,* vol. 368, pp. 558–560 (1994).

Battaglia, M., et al., "Human Enteric Coronaviruses: Further Characterzation and Immunoblotting of Viral Proteins", *The Journal of Infectious Diseases,* vol. 155, No. 1, pp. 140–143 (1987).

Benatti, L., et al., "Two Preproendothelin 1 mRNAs Transcribed by Alternative Promoters," *J. Clin. Invest.,* vol. 91, pp. 1149–1156 (1993).

Bellinger–Kawahara, C., et al., "Complement Component C3 Fixes Selectively to the Major Outer Membrane Protein (MOMP) of *Legionella pneumophila* and Mediates Phgacytosis of Liposome–MOMP Complexes by Human Monocytes", *J. Exp. Med,* vol. 172, pp. 1201–1210 (1990).

Bellon, T., et al., "Identification and expression of two forms of the human transforming growth factor–β–binding protein endoglin with distinct cytoplasmic regions", *Eur. J. Immunol.,* vol. 23, pp. 2340–2345 (1993).

Bensi, G., et al., "An inducible Enhanceer Controls the Expression of the Human Interleukin 1β Gene", *Cell Growth & Differentiation,* vol. 1, pp. 491–497 (1990).

Bensi, G., et al., "Human interleukin–1 beta gene", *Gene,* vol. 52, pp. 95–101 (1987).

Berling, B., et al., "Cloning of a Carcinoembryonic Antigen Gene Family Member Expressed in Leukocytes of Chronic Myeloid Leukemia Patients and Bone Marrow", *Cancer Research,* vol. 50, pp. 6534–6539 (1990).

Bogerd, H.P., et al., "Identification of a Novel Cellular Cofactor for the Rev/Rex Class of Retroviral Regulatory Proteins", *Cell,* vol. 82, pp. 485–494 (1995).

Bonham, K., et al., Organization and analysis of the promoter region and 5'non–coding exons of the human c–src proto–oncogene, *Oncogene,* vol. 8, pp. 1973–1981 (1993).

Bosslet, K., et al., "Molecular and functional and characterisation of a fusion protein suited for tumour specific prodrug activation" *Br. J. Cancer* vol. 65, pp. 234–238 (1992).

Blackwood, E.M., et al., "Max: A Helix–Loop–Helix Zipper Protein That Forms Sequence–Specific DNA–Binding Complex with Myc" *Science,* vol. 251, pp. 1211–1217 (1991).

Blaser, J., "*Helicobacter pylori* and the Pathogenesis of Gastroduodenal Inflammation", *The Journal of Infectious Diseases,* vol. 161, pp. 626–633 (1990).

Burrows, F.J., et al., "Vascular Targeting–A New Approach To The Therapy Of Solid Tumors", *Pharmac. Ther.,* vol. 64, pp. 155–174 (1994).

Brown, F., "Synthetic Peptides and Purified Antigens as Vaccines", *International Journal of Technology Assessment in Health Care,* vol. 10, pp. 161–166 (1994). Brown, D.J., et al., "Redundancy of Signal and Anchor Functions in the $NH_2$–Terminal Uncharged Region of Influenza Virus Neuroaminidase, a Class II Membrane Glycoprotein", *Journal of Virology,* vol. 62, pp. 3824–3831 (1988).

Bryant, C., et al., "Cloning, Nucleotide Sequence, and Expression of the Nitroreductase Gene from *Entrrobacter cloacae*", *The Journal of Biological Chemistry,* vol. 266, pp. 4126–4130 (1991).

Campo, R.E., et al., "M Proteins of Group G Streptococci: Mechanisms of Resistance to Phagocytosis", *The Journal of Infectious Diseases,* vol. 171, pp. 601–606 (1995).

Cassady, A.I., et al., "Isolation and characterization of the genes encoding mouse and human type–5 acid phosphatase", *Gene,* vol. 1340, pp. 201–207 (1993).

Catasus, L., et al., "The Sequence and Conformation of Human Pancreatic Procarboxypeptidase A2", *The Journal of Biological Chemistry,* vol. 270, No. 12, pp. 6651–6657 (1995).

Cerny, A., et al., "The Class 1–Restricted Cytotoxic T Lymphocyte Response to Predetermined Epitopes in the Hepatitis B and C Viruses", *Current Topics in Microbiology and Immunology,* vol. 189, pp. 169–186 (1994).

Chada, S., et al., "Isolation and Chromosomal Localization of the Human Glutathione Peroxidase Gene", *Genomics,* vol. 6, pp. 268–271 (1990).

Chalepakis, G., et al., "Differential Gene Activation by Glucocorticoids and Progestins through the Hormone Regulatory Element of Mouse Mammary Tumor Virus", *Cell,* vol. 53, pp. 371–382 (1968).

Chanock, S.J., et al., "Human Rotaviruses and Genome RNA", *The Journal of Infectious Diseases,* vol. 148, No. 1, pp. 49–50 (1983).

Chasman, D.I., et al., "GAL4 Protein: Purification, Association with GAL80 Protein, and Conserved Domain Structure", *Molecular And Cellular Biology,* vol. 10, pp. 2916–2923 (1990).

Christoffersen, R.E., et al., "Ribozymes as Human Therapeutic Agents", *Journal of Medicinal Chemistry,* vol. 38, No. 12, pp. 2023–2037 (1995).

Clark, et al., "Genomic sequence for human prointerleukin 1 beta; possible evolution from a reverse transcribed prointerleukin 1 alpha gene", *Nucleic Acids Research,* vol. 14, pp. 7897–7914 (1986).

Clissold, P.M., "A cDNA construct of tissue inhibitor of metalloproteinases (TIMP) linked to the last exon of Thy–1 confers glycophospholipid anchorage on this naturally secreted protein", *Biochem J.,* vol. 281, pp. 129–136 (1992).

Cochrane, A.W., et al., "Identification of Sequences Important in the Nucleolar Localization of Human Immunodeficiency Virus Rev: Relevance of Nucleolar Localization to Function", *Journal of Virology,* vol. 64, pp. 881–885 (1990).

Consolo, F., et al., "Nosography and Immunopathogenesis of Viral Hepatitis", *Nephron,* vol. 61, pp. 251–254 (1992).

Coque, J.J.R., et al., "Genes for a β–lactamase, a penicillin–binding protein and a transmembrane protein are clustered with the cephamycin biosynthetic genes in *Nocardia lactamdurans*", *The EMBO Journal,* vol. 12, No. 2, pp. 631–639 (1993).

Cosman, D., et al., "Human Macrophage Colony Stimulating Factor (M–CSF): Alternate RNA Splicing Generates Three Different Proteins that are Expressed on the Cell Surface and Secreted", *Behring Inst. Mitt.,* vol. 83, pp. 15–26 (1988).

Cover, T.L., et al., "Characterization of and Human Serologic Response to Proteins in *Helicobacter pylori* Broth Culture Supernatants with Vacuolizing Cytotoxin Activity", *Infection and Immunity,* vol. 58, No. 3, pp. 603–610 (1990).

Cover, T.L., et al., "Purification and Characterization of the Vacuolating Toxin from *Helicobacter pylon*", *The Journal of Biological Chemistry*, vol. 267, pp. 10570–10575 (1992).

Crabtree, J.E., et al., "Mucosal IgA recoginition of *Helicobacter pylori* 120 kDa protien, peptic ulceration, and gastric pathology", *The Lancet,* vol. 338, pp. 332–334 (1991).

Cruciani, R. A., et al., "Antibiotic magainins exert cytolytic activity against transformed cell lines through channel formation", *Proc. Natl. Acad. Sci. USA,* vol. 88, pp. 3792–3796 (1991).

Cullen, B.R., "Mechanism of Action of Regulatory Proteins Encoded by Complex Retrovirses", *Microbiological Reviews,* vol. 56, pp. 375–394 (1992).

Cunningham, B.A., et al., "The Neutral Cell Adhesion Molecule Structure, Immunoglobulin–Like Domains, Cell Surface Modulation, and Alternative RNA Splicing", *Science,* vol. 236, pp. 799–805 (1987).

Cybulsky, M.I., et al., "Gene structure, chromosomal location, and basis for alternative mRNA splicing of the human VCAM1 gene", *Proc. Natl. Acad. Sci. USA,* vol. 88, pp. 7859–7863 (1991).

Daly, T.J., et al., "Specific binding of HIV–1 recombinant Rev protein to the Rev–responsive element in vitro", *Nature,* vol. 342, pp. 816–819 (1989).

Danielsen, S., et al., "Characterization of the *Escherichia coli codBA* operon encoding cytosine permease and cytosine deaminase", *Molecular Microbiology,* vol. 6, No. 10, pp. 1335–1344 (1992).

De Bruijn, H.L. Maarten, et al., "Human complement component C3: cDNA coding sequence and derived primary structure", *Proc. Natl. Acad. Sci. U.S.A.,* vol. 82, pp. 708–712 (1985).

D'Hondt, E., "Possible approaches to develop vaccines against hepatitis A", *Vaccine,* vol. 10, Suppl. 1, pp. 548–552 (1992).

De Vries, C., et al., "The fms–Like Tyrosine Kinase, a Receptor for Vascular Endothelial Growth Factor", *Science,* vol. 255, pp. 989–991 (1992).

Deonarain, M.P., et al., "Targeting enzymes for cancer therapy: old enzymes in new roles", *Br. J. Cancer,* vol. 70, pp. 786–794 (1994).

Dingermann, T., et al., "RNA polymerase III catalysed transcription can be regulated in *Saccharomyces cerevisiae* by the bacterial tetracycline repressor—operator system", *The EMBO Journal,* vol. 11, pp. 1487–1492 (1992).

Dingermann, T., et al., "Establishment of a System for Conditional Gene Expression Using an Inducible tRNA Suppressor Gene", *Molecular and Cellular Biology,* vol. 12, No. 9, pp. 4038–4045 (1992).

Dingwall, C., et al., "Nuclear targeting sequences—a consensus?," *TIBS,* vol. 16, pp. 478–481 (1991).

Dirks, W., et al., "Dicistronic transcription units for gene expression in mammalian cells", *Gene,* vol. 128, pp. 247–249 (1993).

Dorfman, D.M., et al., "Human Transcription Factor GATA–2", *The Journal of Biological Chemistry,* vol. 267, pp. 1279–1285 (1992).

Drew, P.D., et al., "Cloning and expression analysis of a human cDNA homologous to *Xenopus TFIIIA*", *Gene,* vol. 159, pp. 215–218 (1995).

Du, Run Pan, et al., "A Prototype Recombinant Vaccine Against Respiratory Syncytial Virus and Parainfluenza Virus Type 3" *Bio/Technology,* vol. 12, pp. 813–818 (1994).

Dumont, D.J., et al., "tek, a novel tyrosine kinase gene located on mouse chromosome 4, is expressed in endothelial cells and their presumptive precursors", *Oncogene,* vol. 7, pp. 1471–1480 (1992).

Dunn, B.E., et al., "Purification and Characterization of Urease from *Helicobacter pylon*", *The Journal of Biological Chemistry,* vol. 265, No. 16, pp. 9464–9469 (1990).

Dunn, B.E., et al., "Identification and Purification of a cpn60 Heat Shock Protein Homolog from *Helicobacter pylon*", *Infection and Immunity,* vol. 60, pp. 1946–1951 (1992).

Dyall–Smith, M.L., et al., "Gene–Coding Assignments of Rotavirus Double–Stranded RNA Segments 10 and 11", *Journal of Virology,* vol. 38, pp. 1099–1103 (1981).

Ellis, R.W., "Vaccine Development: Progression From Target Antigen to Product", Genetically Engineered Vaccines, Ciardi et al (ed) Plenum Press, New York vol. 327, pp. 263–271 (1992).

Emerman, M., et al., "The rev Gene Product of the Human Immunodeficiency Virus Affects Envelope–Specific RNA Localization", *Cell,* vol. 57, pp. 1155–1165 (1989).

Enders, B., et al., "Strategies for the development of an antimalarial vaccine", *Vaccine,* vol. 10, pp. 920–927 (1992).

Espersen, F., "Complement Activation By Clumping Factor And Protein A From *Staphylococcus Aureus* Strain E 2371", *Acta Path. Microbiol. Immunol. Scandin.,* Sec 3, vol. 93, pp. 59–64 (1985).

Esteban, J.I., et al., "Hepatitis C: Molecular Biology, Pathogenesis, Epidemiology, Clinical Features, and Prevention", *Progress in Liver Diseases,* vol. 10, pp. 253–282 (1992).

Erzurum, S.C., et al., "Protection of human endothelial cells from oxidant injury by adenovirus–mediated transfer of the human catalase cDNA", *Nucleic Acids Research,* vol. 21, No. 7, pp. 1607–1612 (1993).

Fantozzi, D.A., et al., "The Thermostable Inhibitor of cAMP–dependent Protein Kinase Enhances the Rate of Export of the Kinase Catalytic Subunit from the Nucleus", *The Journal of Biological Chemistry,* vol. 269, pp. 2676–2686 (1994).

Fenton, M.J., "Review: Transcriptional and Post–Transcriptional Regulation of Interleukin 1 Gene Expression", *Int. J. Immunopharmac.,* vol. 14, No. 3, pp. 401–411 (1992).

Fenton, M.J., et al., "Transcriptional Regulation of the Human Prointerleukin 1β Gene", *The Journal of Immunology,* vol. 138, pp. 3972–3979 (1987).

Felber, B.K., et al., "rev protein of human immunodeficiency virus type 1 affects the stability and transport of the viral mRNA", *Proc. Natl. Acad. Sci. USA,* vol. 86, pp. 1495–1499 (1989).

Ferguson, A.J., "Cell–Surface Anchoring of Proteins Via Glycosyl–Phosphatidylinositol Structures", *Ann. Rev. Biochem.,* vol. 57, pp. 285–320 (1988).

Ferreira, V., et al., "The role of the 5'–flanking region in the cell–specific transcription of the human von Willebrand factor gene", *Biochem. J.,* vol. 293, pp. 641–648 (1993).

Fischer, U., et al., "The HIV–1 Rev Activation Domain Is a Nuclear Export Signal That Accesses an Export Pathway Used by Specific Cellular RNAs", *Cell,* vol. 82, pp. 475–483 (1995).

Fischer, U., et al., "Evidence that HIV–1 Rev directly promotes the nuclear export of unspliced RNA", *The EMBO Journal,* vol. 13, No. 17, pp. 4105–4112 (1994).

Fleckenstein, B., et al., "Stage–specific antigens on the surface membrane of sporozoites of malaria parasites" *Nature,* vol. 274, pp. 55–59 (1978).

Flehmig, B., "Hepatitis A", *Bailliere's Clinical Gastroneterology*, vol. 4, No. 3, pp. 707–720 (1990).

Fletcher, M., et al., "Recent Advances in the Understanding of the Biochemisty and Clinical Pharmacology of Interleukin–2", *Lymphokine Research*, vol. 6, No. 1, pp. 45–57 (1987).

Fritzinger, D.C., et al., "Molecular cloning and derived primary structure of cobra venom factor", *Proc. Natl. Acad. Sci. USA*, vol. 91, pp. 12775–12779 (1994).

Fukui, K., et al., "Molecular Cloning and Chromosomal Localization of a Human Gene Encoding D–Amine–acid Oxidase", *The Journal of Biological Chemistry*, vol. 267, No. 26, pp. 18631–18638 (1992).

Furutani, Y., et al., "Complete nucleotide sequence of the gene for human interleukin 1 alpha", *Nucleic Acids Research*, vol. 14, No. 8, pp. 3167–3179 (1986).

Fynan, E.F., et al., "DNA Vaccines: A Novel Approach to Immunization", *Int. J. Immunopharmac*, vol., 17, No. 2, pp. 79–83 (1995).

Galdiero, F., et al., "Activation of Complement System by Porins Extracted from *Salmonella typhimurium*", *Infection and Immunity*, vol. 46, No. 2, pp. 559–563 (1984).

Colbere–Garapin, F.C., et al., "Cloning of the active thymidine kinase gene of herpes simplex virus type 1 in *Escherichia coli* K–12", *Proc. Natl. Acad. Sci, USA*, vol. 76, No. 8, pp. 3755–3759 (1979).

Ge, A.Z., et al., "Cloning and expression of a cDNA encoding mouse endoglin, an endothelial cell TGF–β ligand", *Gene*, vol. 138, pp. 201–206 (1994).

Gibbs, C.P., et al., "Isolation and Structural Mapping of a Human c–src Gene Homologous to the Transforming Gene (v–src) of Rous Sarcoma Virus", *Journal of Virology*, vol. 53, No. 1, pp. 19–24 (1984).

Glass, R.I., et al., "Rotavirus Vaccines: Success by Reassortment?", *Science*, vol. 265, pp. 1389–1391 (1994).

Gough, N.M., et al., "Molecular cloning of cDNA encoding a murine haematopoietic growth regulator, granulocyte–macrophage colony stimulating factor", *Nature*, vol. 309, pp. 763–767 (1984).

Gossen, M., et al., "Control of gene activity in higher eukaryotic cells by prokaryotic regulatory elements", *TIBS*, vol. 18, pp. 471–475 (1993).

Gossen, M., et al., "Transcriptional Activation by Tetracyclines in Mammalian Cells", *Science*, vol. 268, pp. 1766–1769 (1995).

Gatz, C., et al., "Stringent repression and homogeneous de–repression by tetracycline of a modified CaMV 35S promoter in intact transgenic tobacco plants", *The Plant Journal*, vol. 2, pp. 397–404 (1992).

Gum, J.R., et al., "Molecular Cloning of Complementary DNAs Encoding Alkaline Phosphatase in Human Colon Cancer Cells", *Cancer Research*, vol. 50, pp. 1085–1091 (1990).

Haendler, B., et al., "Molecular Cloning of Human Endothelin (ET) Receptors $ET_A$ and $ET_B$", *Journal of Cardiovascular Pharmacology*, vol. 20, pp. S1–S4 (1992).

Hall, B.C., "Prospects for a Respiratory Syncytial Virus Vaccine", *Science*, vol. 265, pp. 1393–1394 (1994).

Hamilton, S., et al., "Cloning and Nucleotide Sequence of the *Salmonella typhimurium dcp* Gene Encoding Dipeptidyl Carboxypeptidase", *Journal of Bacteriology*, vol. 174, No. 5, pp. 1626–1630 (1992).

Haugen, A., et al., "Interleukin–1 Alpha Gene Intron Containing Variable Repeat Region Coding for the SP1 Transcription Factor Recognition Sequences Is Polymorphic", *Molecular Carcinogenesis*, vol. 2, pp. 68–71 (1989).

Harris, J.D., et al., "Gene therapy for cancer using tumour–specific prodrug activation" *Gene Therapy*, vol. 1, pp. 170–175 (1994).

Hawkins, R.E., et al., "A Genetic Approach to Idiotypic Vaccination", *Journal of Immunotherapy*, vol. 14, pp. 273–277 (1993).

Heard, D.J., et al., "Both Arabidopsis TATA binding protein (TBP) isoforms are functionally identical in RNA polymerase II and III transcription in plant cells: evidence for gene–specific changes in DNA binding specificity of TBP", *The EMBO Journal*, vol. 12, No. 9, pp. 3519–3528 (1993).

Heermann, K. H., et al., Large Surface Proteins of Hepatitis B Virus Containing the Pre–s Sequence, *Journal of Viriology*, vol. 52, No. 2, pp. 396–402 (1984).

Henderson, B., et al., "Modulins: A new class of cytokine–inducing, pro–inflammatory bacterial virulence factor", *Inflamm Res*, vol. 44, pp. 187–197 (1995).

Hetherington, S.V., et al., "Complement Component 3 Binding to *Haemophilus influenzae* Type b in the Presence of Anticapsular and Anti–Outer Membrane Antibodies", *Infection and Immunity*, vol. 60, pp. 19–24 (1992).

Hiscott, J., et al., "Characterization of a Functional NF–κB Site in the Human Interleukin 1β Promoter: Evidence for a Postive Autoregulatory Loop", *Molecular and Cellular Biology*, vol. 13, pp. 6231–6240 (1993).

Holzman, L.B., et al., "B61, The ECK Receptor Tyrosine Kinase Ligand is Induced During Mesodermal Differentiation in P19 Embryonal Carcinoma Cells", *J. Am. Soc. Nephrol*, vol. 4, pp. 466, 82P (1993).

Holzman, L.B., et al., "Cloning, Characterization, and Chromosomal Localization of the Human B61 Gene, The ECK Receptor Tyrosine Kinase Ligand", *J. Am. Soc. Nephrol*, vol. 4, pp. 466, 61P (1993).

Honn, K.V., et al., "Adhesion molecules and tumor cell interaction with endothelium and subendothelial matrix", *Cancer and Metastasis Reviews*, vol. 11, pp. 353–375 (1992).

Hoogenboom, H.R., et al., "Building Antibodies from their genes", *Rev. Fr. Transfus. Hemobiol.*, vol. 36, pp. 19–47 (1993).

Hsiao, Ming–Kuang, et al., "Multiple DNA elements are required for the growth regulation of the mouse E2F1 promoter", *Genes & Development*, vol. 8, pp. 1526–1537 (1994).

Huang, J., et al., "A Novel Hepatitis B Virus (HBV) Genetic Element with Rev Response Element–Like Properties That Is Essential for Expression of HBV Gene Products", *Molecular and Cellular Biology*, vol. 13, pp. 7476–7486 (1993).

Huber, B.E., et al., "Retroviral–mediated gene therapy for the treatment of hepatocellular carcinoma: An innovative approach for cancer therapy", *Proc. Natl. Acad. Sci. USA*, vol. 88, pp. 8039–8043 (1991).

Hughes, B.J., et al., "Monoclonal Antibody Targeting of Liposomes to Mouse Lung in Vivo", *Cancer Research*, vol. 49, pp. 6214–6220 (1989).

Hussain, M., et al., "Cloning and Sequencing of the Metallothioprotein β–Lactamase II Gene of *Bacillus cereus* 569H/ in *Escherichia coli*", *Journal of Bacteriology*, vol. 164, pp. 223–229 (1985).

Huston, J.S., et al., "Medical Applications of Single–Chain Antibodies", *Intern. Rev. Immunol.,* vol. 10, pp. 195–217 (1993).

Iademarco, M.F., et al., "Characterization of the Promoter for Vascular Cell Adhesion Molecule–1 (VCAM–1)" *The Journal of Biological Chemistry,* vol. 267, No. 23, pp. 16323–16329 (1992).

Ishida, K., et al., "Nucleotide sequence of a human gene for glutathione peroxidase", *Nucleic Acids Research,* vol. 15, pp. 10051 (1987).

Iwai, S., et al., "Recognition of the high affinity binding site in rev–response element RNA by the Human Immunodeficiency Virus type–1 rev protein", *Nucleic Acids Research,* vol. 20, No. 24, pp. 6465–6472 (1992).

Iwarson, S., "The Main Five Types of Viral Hepatitis: An Alphabetical Update", *Scand J Infect. Dis.,* vol. 24, pp. 129–135 (1992).

Jahroudi, N., et al., "Endothelial–Cell–Specific Regulation of von Willebrand Factor Gene Expression", *Molecular and Cellular Biology,* vol. 14, pp. 999–1008 (1994).

Jacob, L., et al., "Potential therapeutic applications of magainins and other antimicrobial agents of animal origin", *Ciba Foundation Symposium,* vol. 186, pp. 197–223 (1994).

Jarvis, W.D., et al., "Induction of apoptotic DNA damage and cell death by activation of the sphingomyelin pathway", *Proc. Natl. Acad. Sci. USA,* vol. 91, pp. 73–77 (1994).

Jefferson, R.A., et al., "β–Glucuronidase from *Escherichia coli* as a gene–fusion marker", *Proc. Natl. Acad. Sci. USA,* vol. 83, pp. 8447–8451 (1986).

Johnson, D.G., et al., "Autoregulatory control of E2F1 expression in response to positive and negative regulators of cell cycle progression", *Genes & Development,* vol. 8, pp. 1514–1525 (1994).

Jung, M.–C., et al., "T cell recognition of hepatitis B and C viral antigens", *European Journal of Clinical Investigation,* vol. 24, pp. 641–650 (1994).

Katz, S.L., et al., "Measles Vaccine: Do We Need New Vaccines of New Programs?", *Science,* vol. 265, pp. 1391–1392 (1994).

Kaufman, R.J., et al., "Improved vectors for stable expression of foreign genes in mammalian cells by use of the untranslated leader sequence from EMC virus", *Nucleic Acids Research,* vol. 19, No. 16, pp. 4485–4490 (1991).

Kim, Y., et al., "A New Gene with Sequence and Structural Similarity to the Gene Encoding Human Lysyl Oxidase", *The Journal of Biological Chemistry,* vol. 270, No. 13, pp. 7176–7182 (1995).

Kimura, S., et al., "Human thyroid peroxidase: Complete cDNA and protein sequence, chromosome mapping, and identification of two alternately spliced mRNAs", *Proc. Natl. Acad. Sci. USA,* vol. 84, pp. 5555–5559 (1987).

Kinchington, P.R., et al., "The Glycoprotein Products of Varicella–Zoster Virus Gene 14 and Their Defective Accumulation in a Vaccine Strain (Oka)", *Journal of Virology,* vol. 64, No. 9, pp. 4540–4548 (1990).

Kjems, et al., "Structural analysis of the interaction between the human immunodeficiency virus Rev protein and the Rev response element", *Proc. Natl. Acad. Sci. USA,* vol. 88, pp. 683–687 (1991).

Kjems, J., et al., "Specific binding of a basic peptide from HIV–1 Rev", *The EMBO Journal,* vol. 11, No. 3, pp. 1119–1129 (1992).

Knapp, B., et al., "Protection of Aotus Monkeys from Malaria Infection by Immunization with Recombinant Hybrid Proteins", *Infection and Immunity,* vol. 60, No. 6, pp. 2397–2401 (1992).

Kozak, M., "The Scanning Model for Translation: An Update", *The Journal of Cell Biology,* vol. 108, pp. 229–241 (1989).

Lafage, M., et al., "The Human Interleukin–1α Gene Is Located on the Long Arm of Chromosome 2 at Band q13", *Blood,* vol. 73, No. 1 pp. 104–107 (1989).

Lage, P., et al., "H pylori Vacuolating Toxin and Gastroic Cancer", *Acta Gastroenterol. Belg.,* vol. 56 (Suppl.), pp. 61 (1993).

Lam, E.W.–F., et al., "An E2F–binding site mediates cell–cycle regulated repression of mouse B–myb transcription", *The EMBO Journal,* vol. 12, No. 7, pp. 2705–2713 (1993).

Lee, Mu–En, et al., "Cloning of the GATA–binding Protein That Regulates Endothelin–1 Gene Expression in Endothelial Cells", *The Journal of Biological Chemistry,* vol. 266, pp. 16188–16192 (1992).

Lemon, S.M., et al., "Genetic, antigenic and biological differences between strains of hepatitis A virus", *Vaccine,* vol. 10, Suppl. 1, pp. S40–S44 (1992).

Leuther, K.K., et al., "Nondissociation of GAL4 and GAL80 in vivo After Galactose Induction", *Science,* vol. 256, pp. 1333–1335 (1992).

Levine, M.M., et al., "Live oral vaccines against cholera: an update", *Vaccine,* vol. 11, Issue 2, pp. 207–212 (1993).

Lichtenstein, D.L., et al., "Definition and functional analysis of the signal/anchor domain of the human respiratory synctial virus glycoprotein G", *Journal of General Virology,* vol. 77, pp. 109–118 (1996).

Lucibello, F.C., et al., "Periodic cdc25C transcription is mediated by a novel cell cycle–regulated repressor element (CDE)", *The EMBO Journal,* vol. 14, No. 1, pp. 132–142 (1995).

Ludwig, T., et al., "Cloning and sequencing of cDNAs encoding the full–length mouse mannose 6–phosphate/insulin–like growth factor II receptor", *Gene,* vol. 142, pp. 311–312 (1994).

Maddon, P.J., et al., "The Isolation and Nucleotide Sequence of a cDNA Encoding the T Cell Surface Protein T4: A New Member of the Immunoglobulin Gene Family", *Cell,* vol. 42, pp. 93–104 (1985).

Malim, M.H., et al., "Mutational Definition of the Human Immunodeficiency Virus Type 1 Rev Activation Domain", *Journal of Virology,* vol. 65, pp. 4248–4254 (1991).

Malim, M.H., et al., "The HIV–1 rev trans–activator acts through a structured target sequence to activate nuclear export of unspliced viral mRNA", *Nature,* vol. 338, pp. 254–257 (1989).

Malim, M.H., et al., "HIV–1 Structural Gene Expression Requires the Binding of Multiple Rev Monomers to the Viral RRE: Implicatkons for HIV–1 Latency", *Cell,* vol. 65, pp. 241–248 (1991).

Mancuso, V.A., et al., "Posttranscriptional Effector Domains in the Rev Proteins of Feline Immunodeficiency Virus and Equine Infectious Anemia Virus", *Journal of Virology,* vol. 68, No. 3, pp. 1998–2001 (1994).

Mandell, R.B., et al., "Identification of Two HSP70–related Xenopus Oocyte Proteins That Are Capable of Recycling Across the Nuclear Envelope", *The Journal of Cell Biology,* vol. 111, pp. 1775–1783 (1990).

Marasco, W.A., et al., "Design, intracellular expression, and activity of a human anti–human immunodeficiency virus type 1 gp120 single–chain antibody", *Proc. Natl. Acad. Sci. USA*, vol. 90, pp. 7889–7893 (1993).

March, C.J., et al., "Cloning, sequence and expression of two distinct human interleukin–1 complementary DNAs", *Nature*, vol. 315, pp. 641–647 (1985).

Maruyama, K., et al., "Lipid composition is important for highly efficient target binding and retention of immunoliposomes", *Proc. Natl. Acad. Sci. USA*, vol. 87, pp. 5744–5748 (1990).

Matsui, H., et al., "Molecular Cloning and Expression of the Human Interleukin 2 Gene", *Lymphokines*, vol. 12, pp. 1–12 (1985).

Maurice, "Malaria Vaccine Raises a Dilemma", *Science*, vol. 267, pp. 320–323 (1995).

McBurney, M.W., et al., "The mouse Pgk–1 gene promoter contains an upstream activator sequence", *Nucleic Acids Research*, vol. 19, No. 20, pp. 5755–5761 (1991).

Means, A.L., et al., "The HIP1 Binding Site Is Required for Growth Regulation of the Dihydrofolate Reductase Gene Promoter", *Molecular and Cellular Biology*, vol. 12, pp. 1054–1063 (1992).

Melnick, J.L., "Properties and classification of hepatitis A virus", *Vaccine*, vol. 10, Suppl. 1, pp. S24–S26 (1992).

Michael, N.P., et al., "Physical characterisation of the *Escherichia coli* B gene encoding nitroreductase and its over–expression in *Escherichia coli* K12", *FEMBS Microbiol Letters*, vol. 124, pp. 195–202 (1994).

Michenko, A., et al., "Hypoxia Regulatory Elements of the Human Vascular Endothelial Growth Factor Gene", *Cellular and Molecular Biology Research*, vol. 40, No. 1, pp. 35–39 (1994).

Mobley, H.L.T., et al., "*Helicobacter phylori* Urease: Properties and Role in Pathogenesis", *Scand J. Gastroenterol*, vol. 26, Suppl. 187, pp. 39–46 (1991).

Moolten, F.L., "Tumor Chemosensitivity Conferred by Inserted Herpes Thymidine Kinase Genes: Paradigm for a Prospective Cancer Control Strategy", *Cancer Research*, vol. 46, pp. 5276–5281 (1986).

Morgan, R.A., et al., "Retroviral vectors containing putative internal ribosome entry sites: development of a polycistronic gene transfer system and applications to human gene therapy", *Nucleic Acids Research*, vol. 20, No. 6, pp. 1293–1299 (1992).

Mori, N., et al., "Transactivation of the Interleukin–1α Gene Promoter by Human T–Cell Leukemia Virus Type 1 Tax in T Cells", *Blood*, vol. 84, pp. 1688–1689 (1994).

Morishita, K., et al., "A Novel Promoter for Vascular Endothelial Growth Factor Receptor (flt–1) That Confers Endothelial–specific Gene Expression", *J. Biol. Chem.*, vol. 270, pp. 27948–27953 (1995).

Morrissey, J.H., et al., "Molecular Cloning of the cDNA for Tissue Factor, the Cellular Receptor for the Initiation of the Coagulation Protease Cascade", *Cell*, vol. 50, pp. 129–135 (1987).

Muesing, M.A., et al., "Nucleic acid structure and expression of the human AIDS/lymphadenopathy retrovirus" *Nature*, vol. 313, pp. 450–458 (1985).

Mukhopadhyay, et al., "Hypoxic induction of human vascular endothelial growth factor expression through c–Src activationp", *Nature*, vol. 375, pp. 577–581 (1995).

Mullen, C.A., "Metabolic Suicide Genes in Gene Therapy", *Pharmac. Ther.*, vol. 63, pp. 199–207 (1994).

Mullen, C.A., et al., "Transfer of the bacterial gene for cytosine deaminase to mammalian cells confers lethal sensitivity to 5–fluorocytosine: A negative selection system", *Proc. Natl. Acad. Sci. USA*, vol. 89, pp. 33–37 (1992).

Murakami, T., et al., "Identification of Two Enhancer Elements in the Gene Encoding the Type 1 Glucose Transporter from the Mouse Which Are Responsive to Serum, Growth Factor, and Oncogenes", *The Journal of Biological Chemistry*, vol 267, pp. 9300–9306 (1992).

Neish, A.S., et al., "Endothelial Interferon Regulatory Factor 1 Cooperates with NF–κB as a Transcriptional Activator of Vascular Cell Adhesion Molecule 1", *Molecular and Cellular Biology*, vol. 15, pp. 2558–2568 (1995).

Neish, A.S., et al., "Functional Analysis of the Human Vascular Cell Adhesion Molecule 1 Promoter", *J. Exp. Med.*, vol. 176, pp. 1583–1593 (1992).

Nicola, N.A., et al., "Similar Molecular Properties of Granulocyte–Macrophage Colony–stimulating Factors Produced by Different Mouse Organs in Vitro and in Vivo", *The Journal of Biological Chemistry*, vol. 254, No. 12, pp. 5290–5299 (1979).

Nussenzweig, R.S., et al., "Malaria Vaccines: Multiple Targets", *Science*, vol. 265, pp. 1381–1383 (1994).

O'Keefe, M.C., et al., "A Novel Cleavage Product of Human Complement Component C3 with Structural and Functional Properties Cobra Venoma Factor", *The Journal of Biological Chemistry*, vol. 263, No. 25, pp. 12690–12697 (1988).

O'Reilly, M.S., et al., "Angiostatin induces and sustains dormancy of human primary tumors in mice", *Nature Medicine*, vol. 2, No. 6, pp. 689–692 (1996).

Oshima, A., et al., "Cloning, sequencing, and expression of cDNA for human β–glucuronidase", *Proc. Natl. Acad. Sci. USA*, vol. 84, pp. 685–689 (1987).

Oshima, A., et al., "The Human Cation–independent Mannose 6–Phosphate Receptor", *The Journal of Biological Chemistry*, vol. 263, pp. 2553–2562 (1988).

Osterman, A.L., et al., "Primary Structure of Carboxypeptidase T: Delineation of Functionally Relevant Features in Zn–Carboxypeptidase Family", *Journal of Protein Chemistry*, vol. 11, No. 5, pp. 561–570 (1992).

Pandey, A., et al., "Role of B61, the Ligand for the Eck Receptor Tyrosine Kinase, in TNF–α–Induced Angiogenesis", *Science*, vol. 268, pp. 567–569 (1995).

Parker, R.C., et al., "Isolation of Duplicated Human c–src Genes Located on Chromosomes 1 and 20", *Molecular and Cellular Biology*, vol. 5, pp. 831–838 (1985).

Partanen, J., et al., "A Novel Endothelial Cell Surface Receptor Tyrosine Kinase with Extracellular Epidermal Growth Factor Homology Domains", *Molecular and Cellular Biology*, vol. 12, pp. 1698–1706 (1992).

Pauli, B.U., et al., "Organ–preference of metastasis", *Cancer and Metastasis Reviews*, vol. 9, pp. 175–189 (1990).

Peck–Miller, K.A., et al., "Identification of serum components that inhibit the tumoricidal activity of amphiphillic alpha helical peptides", *Cancer Chemother. Pharmacol.*, vol. 32, pp. 109–115 (1993).

Pelletier, J., et al, "Internal initiation of translation of eukaryotic mRNA directed by a sequence derived from poliovirus RNA", *Nature*, vol. 334, pp. 320–325 (1988).

Perlmutter, R.M., et al., "Structure and Expression of Ick Transcripts in Human Lymphoic Cells" *Journal of Cellular Biochemistry*, vol. 38, pp. 117–126 (1988).

Piñol–Roma, S., et al., "Shuttling of pre–mRNA binding proteins between nucleus and cytoplasm", *Nature,* vol. 355, pp. 730–732 (1992).

Plate, K.H., et al., "Vascular Endothelial Growth Factor and Glioma Angiogenesis: Coordinate Induction of VEGF Receptors, Distribution of VEGF Protein And Possible In Vivo Regulatory Mechanisms", *Int. J. Cancer,* vol. 59, pp. 520–529 (1994).

Plate, K.H., et al., "Molecular Mechanisms of Developmental and Tumor Angiogenesis", *Brain Pathology,* vol. 4, pp. 207–218 (1994).

Plotkin, S.A., "Vaccines for Varicella–Zoster Virus and Cytomegalovirus: Recent Progress", *Science,* vol. 265, pp. 1383–1385 (1994).

Pohlmann, R., et al., "Cloning of a cDNA encoding the human cation–dependent mannose 6–phosphate–specific receptor" *Proc. Natl. Acad. Sci. USA,* vol. 84, pp. 5575–5579 (1987).

Pusztai, L., et al., "Growth Factors: Regulation of Normal and Neoplastic Growth", *Journal of Pathology,* vol. 169, pp. 191–201 (1993).

Ratner, L., et al., "Complete nucleotide sequence of the AIDS virus, HTLV–III", *Nature,* vol. 313, pp. 277–284 (1985).

Rehemtulla, A., et al., "High Level Expression of Recombinant Human Tisue Factor in Chinese Hamster Ovary Cells as a Human Thromboplastin", *Thromb. Haemost.,* vol. 65, pp. 521–527 (1991).

Reynolds, D.S., et al., "Cloning and Characterization of the Novel Gene for Mast Cell Carboxypeptidase A", *J. Clin. Invest.,* vol. 89, pp. 273–282 (1992).

Robinson, H.L., et al., "Protection against a lethal influenza virus challenge by immunization with a haemagglutinin–expressing plasmid DNA", *Vaccine,* vol. 11, Issue 9, pp. 957–960 (1993).

Riechmann, L., et al., "Reshaping human antibodies for therapy", *Nature,* vol. 332, pp. 323–327 (1988).

Rodrigues, M.L., et al., "Development of a Humanized Disulfide–stabilized Anti–p185$^{HER2}$ Fv–β–Lactamase Fusion Protein for Activation of a Cephalosporin Doxorubicin Prodrug", *Cancer Research,* vol. 55, pp. 63–70 (1995).

Sakamaki, K., et al., "Molecular Cloning and Characterization of a Chromosomal Gene for Human Eosinophil Peroxidase", *The Journal of Biological Chemistry,* vol. 264, No. 28, pp. 16828–16836 (1989).

Scarpati, E.M., et al., "Human Tissue Factor: cDNA Sequence and Chromosome Localization of the Gene", *Biochemistry,* vol. 26, pp. 5234–5238 (1987).

Schaible, U.E., "Distinct patterns of protective antibodies are generated against *Borrelia burgdorferi* in mice experimentally inoculated with high and low doses of antigen", *Immunology Letters,* vol. 36, pp. 219–226 (1993).

Schnürch H., et al., "Expression of tie–2, a member of a novel family of receptor tyrosine kinases, in the endothelial cell lineage", *Development,* vol. 119, pp. 957–968 (1993).

Schrewe, H., et al., "Cloning of the Complete Gene for Carcinoembryonic Antigen: Analysis of Its Promoter Indicates a Region Conveying Cell Type–Specific Expression", *Molecular and Cellular Biology,* vol. 10, pp. 2738–2784 (1990).

Schulz, M., et al., "Partial Purification and Characterization of a Luteolin–Triglucuronide–Specific β–Glucuronidase From Rye Primary Leaves (*Secale Cereale*)", *Phytochemistry,* vol. 26, No. 4, pp. 933–937 (1987).

Selvaraj, P., et al., "The major Fc receptor in blood has a phosphatidylinositol anchor and is deficient in paroxysmal nocturnal haemoglobinuria", *Nature,* vol. 333, pp. 565–567 (1988).

Semenza, G.L., et al., "Hypoxia–inducible nuclear factors bind to an enhancer element located 3'to the human erythropoietin gene", *Proc. Natl. Acad. Sci. USA,* vol. 88, pp. 5680–5684 (1991).

Senger, D.R., "Vascular permeability factor (VPF, VEGF) in tumor biology", *Cancer and Metastasis Reviews,* vol. 12, pp. 303–324 (1993).

Shipley, J.M., et al., "The Role of Glycosylation and Phosphorylation in the Expression of Active Human β–Glucuronidase", *The Journal of Biological Chemistry,* vol. 268, pp. 12193–12198 (1993).

Simpson, S.C., et al., "CD4 and p56$^{lck}$ can stabley associate when co–expressed in NIH3T3 cells" *Oncogene,* vol. 4 pp. 1141–1143 (1989).

Snoeck, R., et al., "Chemotherapy of varicella zoster virus infections", *International Journal of Antimicrobial Agents,* vol. 4, pp. 211–226 (1994).

Song, Q., et al., "Cloning and characterization of a human protein phosphatase 1 encoding cDNA", *Gene,* vol. 129, pp. 291–295 (1993).

Spicer, E.K., et al., "Isolation of cDNA clones coding for human tissue factor: Primary structure of the protein and cDNA", *Proc. Natl. Acad. Sci. USA,* vol. 84, pp. 5148–5152 (1987).

Strubin, M., et al., "Yeast and Human TFIID with Altered DNA–Binding Specificity for TATA Elements", *Cell,* vol. 68, pp. 721–730 (1992).

Sugitomo, Yu., et al., "Efficient Expression of Drug–selectable Genes in Retroviral Vectors Under Control of an Internal Ribosome Entry Site", *Bio/Technology,* vol. 12, pp. 694–698 (1994).

Tailor, P.G., et al., "Nucleotide sequence of human prostatic acid phosphatase determined form a full–length cDNA clone", *Nucleic Acids Research,* vol. 18, No. 16, p. 4928 (1990).

Taniguchi, T., et al., "Structure and expression of a cloned cDNA for human interleukin–2", *Nature,* vol. 302, pp. 305–310 (1983).

Ten, R.M., et al., "Molecular Cloning of the Human Eosinophil Peroxidase", *J. Exp. Med.,* vol. 169, pp. 1757–1769 (1989).

Terman, B.I., et al., "Identification of the KDR Tyrosine Kinase as a Receptor for Vascular Endothelial Cell Growth Factor" *Biochemical and Biophysical Research Communications,* vol. 187, No. 3, pp. 1579–1586 (1992).

Tiley, L.S., et al., "Conserved Functional Organization of the Human Immunodeficiency Virus Type 1 and Visna Virus Rev Proteins" *Journal of Virology,* vol. 65, pp. 3877–3881 (1991).

Tindle, R.W., et al., "Immune Response to Human Papillomaviruses and the Prospects for Human Papillomavirus–Specific Immunisation", *Current Topics in Microbiology and Immunology,* vol. 186, pp. 217–253 (1994).

Tischer, E., et al., "The Human Gene for vascular Endothelial Growth Factor", *The Journal of Biological Chemistry,* vol. 266, pp. 11947–11954 (1991).

Triezenberg, S.J., et al., "Functional dissection of VP16, the trans–activator of herpes simplex virus immediate early gene expression", *Genes & Development,* vol. 2, pp. 718–729 (1988).

Triezenberg, S.J., "Sturcture and function of transcriptional activation domains", *Current Opinion in Genetics and Development*, vol. 5, pp. 190–196 (1995).

Truss, M., et al., "Steroid Hormone Receptors: Interaction with Deoxyribonucleic Acid and Transcription Factors", *Endocrine Reviews*, vol. 14, 459–479 (1993).

Turner, J.M., et al., "Interaction of the Unique N–Terminal Region of Tyrosine Kinase p56$^{lck}$ with Cytoplasmic Domains of CD4 and CD8 Is Mediated by Cysteine Motifs", *Cell*, vol. 60, pp. 755–765 (1990).

Turner, M., et al., "Regulation of Expression of Human IL–1α and IL–1β Genes", *The Journal of Immunology*, vol. 143, pp. 3556–3561 (1989).

Ulmer, J.B., et al., "Heterologous Protection Against Influenza by Injection of DNA Encoding a Viral Protein", *Science*, vol. 259, pp. 1745–1749 (1993).

Valenzuela, P., et al., "Nucleotide sequence of the gene coding for the major protein of hepatitis B virus surface antigen", *Nature*, vol. 280, pp. 815–819 (1979).

van der Geer, P., et al., "Receptor Protein–Tyrosine Kinase and Their Signal Transduction Pathways", *Ann. Rev. Cell Biol.*, vol. 10, pp. 251–337 (1994).

Varner, J.A., et al., "The Integrin $α_{w}β_{3}$: Angiogenesis and Apoptosis", *Cell Adhesion and Communication*, vol. 3, pp. 367–374 (1995).

Venkatesh, L.K., et al., "Mutants in a Conserved Region near the Carboxy–Terminal of HIV–1 Rev Identify Functionally Important Residues and Exhibit a Dominant Negative Phenotype", *Virology*, vol. 178, pp. 327–330 (1990).

Vijaya, S., et al., "Transport to the Cell Surface of a Peptide Sequence Attached to the Truncated C Terminus of an N–Terminally Anchored Integral Membrane Protein", *Molecular and Cellular Biology*, vol. 8, No. 4, pp. 1709–1714 (1988), Vile, R.G., et al., "Use of Tissue–specific Expression of the Herpes Simplex Virus Thymidine Kinase Gene to Inhibit Growth of Established Murine Melanomas following Direct Intratumoral Injection of DNA", *Cancer Research*, vol. 53, pp. 3860–3864 (1993).

Wagner, M.J., et al., "Nucleotide sequence of the thymidine kinase gene of herpes simplex virus type 1", *Proc. Natl, Acad. Sci. USA*, vol. 78, pp. 1441–1445 (1981).

Wakiya, K., et al., "Characterization of the Promoter Region for FLT–1 Tyrosine Kinase (VEGF Receptor 1) Gene", *J. Vascular Res.*, vol. 33, pp. 105 (1998).

Wallich, R., et al., "Genotypic variation of Borrelia burgdorferi: Consequences for diagnosis in molecular biology", *Lab. Med.*, vol. 17, pp. 269–276 (1993) Article in German; only Abstract considered.

Wang, B., et al., "Gene inoculation generated immune responses against human immunodeficiency virus type 1", *Proc. Natl. Acad. Sci. USA*, vol. 90, pp. 4156–4160 (1993).

Watanabe, M., et al., "Nucleotide sequence of *Salmonella typhimurium* nitroreductase gene", *Nucleic Acids Research*, vol. 18, No. 4, p. 1059 (1990).

Webb, M.L., et al., "Cloning and Expression of an Endothelin Receptor Subtype B from Human Prostate that Mediates Contration", *Molecular Pharmacology*, vol. 47, pp. 730–736 (1995).

Wen, W., et al., "Heat–stable Inhibitors of cAMP–dependent Protein Kinase Carry a Nuclear Export Signal", *The Journal of Biological Chemistry*, vol. 269, pp. 32214–32220 (1994).

Wen, W., et al., "Identification of a Signal for Rapid Export of Proteins from the Nucleus", *Cell*, vol. 82, pp. 463–473 (1995).

Westerink, M.A.J., et al., "Anti–idiotypic antibodies as vaccines against carbohydrate antigens", *Springer Semin Immunopathol*, vol. 15, pp. 227–234 (1993).

Wilson, D.B., et al., "A Nonerythroid GATA–Binding Protein is Required for Funcrtion of the Human Preproendothelin–1 Promoter in Endothelial Cells", *Molecular and Cellular Biology*, vol. 10, pp. 4854–4862 (1990).

Winter, G., et al., "Man–made antibodies", *Nature* vol. 349, pp. 293–299 (1991).

Wong, G.G., "Human GM–SCF: Molecular Cloning of the Complementary DNA and Purification of the Natural and Recombinant Proteins", *Science*, vol. 228, pp. 810–815 (1995).

Yamamoto, K.K., et al., "Isolation of a cDNA Encoding a Human Serum Marker for Acute Pancreatitis", *The Journal of Biological Chemistry*, et al., vol. 267, pp. 2575–2581 (1992).

Ye, K., et al., "Identification of the Promoter region of human interleukin 1 type 1 receptor gene: Multiple initiation sites, high G+C content, and constitutive expression", *Proc. Natl. Acad. Sci, USA*, vol. 90, pp. 2295–2299 (1993).

Zapp, M.J., et al., "Sequence–specific RNA binding by the HIV–1 Rev protein", *Nature*, vol. 342, pp. 714–716 (1989).

Zwicker, J., et al., Cell cycle regulation of the cyclin A, cdc25C and cdc2 genes is based on a common mechanism of transcriptional repression, *The EMBO Journal*, vol. 14, pp. 4514–4522 (1995).

Zwicker, J., et al., "Cell cycle Regulation of cdc25C transcription is mediated by the periodic repression of the glutamine–rich activators NF–Y and SP 1", *Nucleic Acids Research*, vol. 23, pp. 3822–3830 (1995).

Zwicker, J., et al., "Cell Cycle regulation of E2F Site Occupation in Vivo", *Science*, vol. 271, pp. 1595–1597 (1996).

* cited by examiner

Figure 5A

F) | Component a) | Component b) | Component h) | Component c) | Component d) | Component i) | Component k) |

5'— | Promoter or enhancer sequence I | Structural genes containing a mutation for inhibiting the expression or the function of the encoded protein | Nuclear retention signal (NRS) | Promoter or enhancer sequence II | Gene for a tRNA or a protein for relieving the mutation in component b) | Promoter or enhancer sequence III | Nuclear export factor (NEF) | —3'

Figure 5B

G) | Component a') | Component b) | Component h) | Component c) | Component d') | Component i) | Component k) |

5'— | Promoter or enhancer sequence I containing a mutation for inhibiting the function | Structural gene | Nuclear retention signal (NRS) | Promoter or enhancer sequence II | Gene for a protein for relieving the mutation in component a') | Promoter or enhancer sequence III | Nuclear export factor (NEF) | —3'

Figure 6

H) | Component a') | Component b) | Component h) | Component c) | Component d) | Component i) | Component k) | Component e) | Component d') |

5'— | Promoter or enhancer sequence I containing a mutation for inhibiting the function | Structural gene containing a mutation for inhibiting the expression or the function of the encoded protein | Nuclear retention signal (NRS) | Promoter or enhancer sequence II | Gene for a tRNA or a protein for relieving the mutation in component b) | Promoter or enhancer sequence III | Nuclear export factor (NEF) | Promoter or enhancer sequence IV | Gene for a protein for relieving the mutation in component a') | —3'

(N = nucleotide sequence; AA = amino acid sequence)

Fusion protein of the activator subunit A

Fusion protein of the activator subunit B

NUCLEIC ACID CONSTRUCTS CONTAINING HYBRID PROMOTERS

BACKGROUND OF THE INVENTION

The present application relates to nucleic acid constructs which can be used in genetic manipulation and in particular in the prophylaxis or therapy of diseases (termed gene therapy in that which follows). In gene therapy, genes which are to be expressed in an organism are introduced into the organism. The regulation of the expression of these genes is of significance for the prophylactic or therapeutic effect of the gene therapy.

Regulators of the expression of a gene are described in Patent Applications PCT/GB95/02000, PCT/EP95/03370, PCT/EP95/03371, PCT/EP95/03368 and PCT/EP95/03339. These regulators comprise an activator sequence whose function is, for example, the cell-specific or virus-specific activation of basal transcription. The DNA sequence of this activator sequence is linked by its 3' end to the 5' end of a promoter module. The structural gene is in turn linked by its 5' end to the 3' end of the promoter module.

The promoter module is composed of nucleic acid sequences for binding the transcription factors of the CDF and CHF families or of the E2F and CHF families. In the G0 and G1 phases of the cell cycle, this binding leads to inhibition of the upstream activator sequence and consequently to inhibition or transcription of the structural gene which is located downstream (i.e. in the direction of transcription).

In the G0 and G1 phases of cell division, the DNA which is contained in the cell is in the diploid state. In the G0 phase, the cell is at rest, while in the G1 phase its cell cycle progression is inhibited. The G1 phase is followed by the S phase, in which DNA synthesis takes place and in which the genome is replicated. There then follows the G2 phase, in which the cell is in the tetraploid state. The G2 phase is followed by cell division (mitosis=M phase). The daughter cells then pass into the G0 state or G1 state.

The combination of a cell-specific or virus-specific activator sequence and a promoter module which inhibits this activator sequence in the G0 and G1 phases consequently makes it possible to regulate the expression of a structural gene in a cell-specific or virus-specific and also cell cycle-specific (i.e. restricted to the S and G2 phases) manner.

The combination of an activator sequence and a promoter module is termed a chimeric promoter. While there are many possible applications for chimeric promoters in gene therapy, there are also a number of limitations arising from shortcomings. Examples of these limitations are:

- a weak activator sequence which brings about too low a transcription of the structural gene,
- the use of an activator sequence which cannot be inhibited by the chosen promoter module in a sufficiently cell cycle-dependent manner,
- the restriction to two (for example cell-specific or virus-specific and cell cycle-specific) regulators of the transcription of the structural gene, and
- inadequate intracellular transport of the transcription product of the structural gene which has been introduced into the cell.

The present invention overcomes the shortcomings of using known chimeric promoters to express foreign genes by providing the nucleic acid constructs of the present invention, which enable the regulated expression of foreign genes in host cells.

SUMMARY OF THE INVENTION

An object of the present invention is to make available nucleic acid constructs which enable the expression of foreign genes (transgenes) to be regulated in a precise manner in the host cells. The present invention therefore relates to nucleic acid constructs in which precise regulation of the transgene is achieved by at least one nucleic acid sequence exhibiting a first mutation which inhibits the proper expression of a transgene, and in which at least one further nucleic acid sequence exhibits a second mutation which abolishes the inhibition due to the mutation in the first nucleic acid sequence(s).

More particularly, the nucleic acid construct of the present invention regulates expression of a transgene in a host cell utilizing alternative constructs. When the nucleic acid sequence containing the first mutation is a transgene (b) containing a mutation which inhibits the transcription and/or the translation of said transgene or inhibits the function of the pharmacologically active compound, then the nucleic acid construct further comprises a first promoter or enhancer sequence (a), which is located upstream from the 5' end of the transgene, or alternatively, when the nucleic acid sequence containing the first mutation is a first promoter or enhancer sequence (a'), which contains a mutation which inhibits the function of the first promoter, then the nucleic acid construct further comprises a transgene (b') encoding a pharmacologically active compound. In either instance, at least one nucleic acid sequence containing the second mutation abolishes the inhibition due to the first mutation.

These nucleotide sequences are under the control of identical or different promoter sequences, so that a transgene can only be expressed when all these promoter sequences are activated.

Preferably, the novel nucleic acid constructs comprise at least the following components, listed in the direction of reading, from the 5' end to the 3' end:

- a first (I) promoter or enhancer sequence (a) which is nonspecific, cell-specific or virus-specific, or which can be activated by tetracycline or metabolically and/or cell cycle-specifically, which activates the transcription of a transgene and which can contain a mutation (a') which inhibits the function of the promoter,
- a transgene (b') which, as structural gene, encodes an active compound and can contain a mutation (b) which stops the transcription and/or the translation of this structural gene or inhibits the function of the product of the structural gene,
- a second (II) promoter or enhancer sequence (c) or (c') which is nonspecific, cell-specific or virus-specific, or which can be activated metabolically and/or cell cycle-specifically, which activates the basal transcription of the component (d) or (d') and which can contain a mutation which inhibits the function of the promoter,
- a gene for a tRNA (suppressor tRNA) or a regulatory protein (d) or (d') for relieving the mutation in one or more of the promoters or in the transgene.

The first (I) promoter sequence or enhancer sequence (a) and the second (II) promoter sequence or enhancer sequence (c) can be identical or different, and at least one of the components (a) and (c) can be nonspecifically, cell-specifically or virus-specifically activatable, be activatable by tetracycline or metabolically, in particular by hypoxia, or be cell cycle-specifically activatable.

The invention also relates to a nucleic acid construct wherein the component (b) exhibits a nuclear retention signal whose cDNA is linked, at the 5' end, directly or indirectly, to the 3' end of the structural gene, and wherein the transcription product of the nuclear retention signal exhibits a structure for binding a nuclear export factor.

The invention also relates to a nucleic acid construct which, in addition to components (a) to (d), exhibits the following components:

a further promoter or enhancer sequence (i) which activates the basal transcription of a nuclear export factor, and a nucleic acid which encodes a nuclear export factor (k) which binds to the transcription product of the nuclear retention signal (h) and thereby mediates transport of the transcription product of the transgene out of the cell nucleus into the cytoplasm.

Within the context of the present invention, at least one of the promoter sequences or enhancer sequences (a) and (c) can be a chimeric promoter in which the promoter module CDE-CHR or E2FBS-CHR can interact with an upstream activator sequence which is cell-specifically, virus-specifically or metabolically activatable and can thereby influence, in particular inhibit, the expression of a downstream gene.

The components (a) and (c) can also be activator-responsive promoter units. Such constructs also exhibit the following components:

at least one promoter or enhancer sequence (e) which can be activated nonspecifically, virus-specifically, metabolically, by tetracycline, or cell-specifically and/or cell cycle-specifically, at least one activator subunit (f) which is situated downstream of the promoter or enhancer sequence (e) and whose transcription is activated by the promoter or enhancer sequence (e), and an activator-responsive promoter (g) which is activated by the expression products of an activator subunit as described in (f) or of several identical or different activator subunits In a further embodiment of the invention the nucleic acid constructs are nucleic acid constructs in which the promoter sequence or enhancer sequence (a) and/or (c) and/or (i) and/or the activator-responsive promoter (g) is a chimeric promoter and the activator subunit (f) is a gene for at least one transcription factor which activates the chimeric promoter of the activator-responsive promoter (g).

The invention also relates to a nucleic acid construct which contains an activator-responsive promoter (g) which is activated by two activator subunits (f, f'); e.g., the LexA operator (monomers or multimers) in conjunction with the SV40 promoter. The activator subunit (f) comprises the cDNA for the LexA DNA-binding protein, encoding amino acids 1–81 or 1–202, whose 3' end is linked to the 5' end of the cDNA for the Gal80 protein (amino acids 1–435). The second activator subunit (f') comprises the cDNA of the Gal80-binding domain of the Gal4 protein, encoding amino acids 851–881, whose 3' end is linked to the 5' end of the cDNA of the SV40 large T antigen, encoding amino acids 126–132, whose 3' end is linked to the 5' end of the cDNA for the transactivating domain of HSV-1 VP16, encoding amino acids 406–488.

In another example of an activator-responsive promoter (g) which is activated by two activator subunits (f, f'), the above mentioned LexA operator is replaced with the Gal4-binding region (singly or arranged multiply in succession) and the gene for the LexA DNA-binding protein is replaced with the gene for the DNA-binding domain (AA1 to 147) of the Gal4 protein.

The invention also relates to a nucleic acid construct which contains, as the activator-responsive promoter (g), monomers and multimers of the binding sequence for the Gal4 binding protein, and the activator subunit (f) contains the nuclear localization signal (NLS) of SV40 (SV40 large T; amino acids 126–132; PKKKRKV, SEQ ID NO.: 1), the acid transactivating domain (TAD) from HSV-1 VP16 (amino acids 406488) and the cDNA for the cytoplasmic moiety of the CD4 glycoprotein (amino acids 397–435), and the activator subunit (f) contains the nuclear localization signal (NLS) of SV40 (SV40 large T; amino acids 126–132; PKKKRKV; SEQ ID NO. 1), the cDNA for the DNA-binding domain of the Gal4 protein (amino acids 1–147) and the cDNA for the CD4-binding sequence of the p56 lck protein (amino acids 1–71).

In another example of an activator-responsive promoter unit in which the activator-responsive promoter (g) is the binding sequence for Gal4, the cDNA for the Gal80 protein (amino acids 1435) in the activator subunit (f) is replaced with the cDNA for the cytoplasmic moiety of the CD4 glycoprotein (amino acids 397–437; Simpson et al., Oncogene 4: 1141 (1989); Maddon et al., Cell 42: 93 (1985)) and the cDNA of the Gal80-binding domain of the Gal4 protein (encoding amino acids 851–881) in the activator subunit (f) is replaced with the cDNA for the CD4-binding sequence of the p56 lck protein (amino acids 1–71; Shaw et al., Cell 59: 627 (1989); Turner et al., Cell 60: 755 (1990); Perlmutter et al., J. Cell. Biochem. 38: 117 (1988)).

In a further preferred embodiment, the novel nucleic acid construct can exhibit a nuclear retention signal (NRS) which is linked, downstream in the reading direction (i.e. by the 5' end of its DNA), to a transgene (b), (i.e. at the 3' end of the transgene).

In another preferred embodiment, the transcription product of the nuclear retention signal has a structure for binding a nuclear export factor (NEF). The cDNA for this nuclear export factor is preferably linked, by its 5' end, to the 3' end of another promoter sequence or enhancer sequence which can be identical to or different from the promoter sequences (a) and/or (c).

The nuclear export factor (k) is preferably a gene which is selected from the group consisting of the rev gene of retroviruses such as the HIV-1 or HIV-2 viruses, visna-maedi virus, caprine arthritis encephalitis virus, equine infectious anemia virus, feline immunodeficiency virus or HTLV, or the gene for the hnRNP-A1 protein, or the gene for the transcription factor TFIII-A.

As a rule, the nucleic acid is DNA. The novel nucleic acid constructs are customarily employed as vectors, in particular plasmid vectors (non-viral) or viral vectors.

As a rule, the transgene is a structural gene which encodes a pharmacologically active compound which is selected from the group consisting of cytokines, interferons, growth factors, antibodies or antibody fragments, receptors for cytokines or growth factors, proteins having an antiproliferative or cytostatic effect, enzymes, angiogenesis inhibitors, thrombosis-inducing substances and coagulation inhibitors, proteins having a fibrinolytic effect, blood plasma proteins, complement-activating proteins, virus coat proteins, bacterial antigens and parasitic antigens, tumor antigens, proteins having an effect on the blood circulation, peptide hormones and ribonucleic acids, such as ribozymes and antisense RNA.

In a particular embodiment, the transgene can be a structural gene which encodes a protein which triggers controlled cell death. An example of these proteins is sphingomyelinase.

In another embodiment, the transgene (b) can be a structural gene which encodes an enzyme which cleaves a precursor of a drug to form a drug. In a particular embodiment, the transgene can be a structural gene which encodes a fusion protein which is composed of a ligand and one of the previously mentioned proteins or peptide active compounds. The ligand can, for example, be an antibody, an antibody fragment, a cytokine, a growth factor, a peptide hormone or a receptor. In a particular embodiment, the structural gene can encode a ligand-enzyme fusion protein, with the enzyme cleaving a precursor of a drug, thereby forming a drug, and the ligand binding to a cell surface, preferably on endothelial cells or tumor cells.

The promoter sequence, enhancer sequence or activator sequence can be selected from the group of gene-regulatory nucleotide sequences which activate in endothelial cells, smooth muscle cells, striated muscle cells, macrophages, lymphocytes, tumor cells, liver cells, leukemia cells and glia cells, or of promoter sequences from the HBV, HCV, HSV, HPV, EBV, HTLV or HIV viruses.

The activator sequence can furthermore be a tetracycline operator in combination with a corresponding repressor.

The invention relates to viral or non-viral vectors which contain a novel nucleic acid construct and which are locally or perorally administered to, or injected into patients. Additionally the novel nucleic acid construct can also be administered intravenously, intraarterially, into a body cavity, into an organ or subcutaneously.

The invention also relates to isolated cells or cell lines which harbor a novel nucleic acid construct and which are locally administered to, or injected into patients.

Examples of such cells are tumor cells, immune cells such as a macrophage or a lymphocyte, or endothelial cells. Cells of this nature can also be used for preparing a pharmaceutical for treating a disease, with the preparation of the pharmaceutical comprising the introduction of the nucleic acid construct into a target cell.

The novel nucleic acid constructs allow any promoters, enhancers or activator sequences to be used.

The novel mutation in or on the transgene (b) can be the replacement of the nucleic acid sequence for one or more amino acids such that, as a result of this replacement, the expressed protein is no longer capable of functioning. In this case, the component (d) is a nucleic acid sequence which encodes a tRNA which, on the one hand, binds by its anticodon to the mRNA of the mutated nucleotide sequence in the transgene (b) and, on the other hand, carries an end group which takes up the correct amino acid for relieving the mutation in the transgene (b).

However, the novel mutation in or on the transgene (b) can also be a translation stop codon in the structural gene, which codon is either not found or only rarely found in mammalian cells, such that the structural gene is not effectively translated. In this case, the component (d) is a nucleic acid sequence which, on the one hand, encodes a tRNA which possesses an anticodon which is complementary to the stop codon and thereby relieves the inhibition of the translation which is due to the translation stop codon in the structural gene (b) and, on the other hand, carries an end group which takes up the correct amino acid for relieving the mutation in the transgene (b).

In another embodiment, the mutation in or on the transgene (b) can be a mutation of the TATA box of a promoter sequence which is located upstream of the 5' end of the structural gene. This mutation blocks the initiation of the transcription of the structural gene. In this case, the component (d) is a nucleic acid sequence which encodes a protein which binds to the mutated TATA box and thereby enables transcription to take place.

The present invention is further directed to a method of inhibiting cell proliferation by contacting cells with a cell proliferation inhibiting amount of the nucleic acid construct containing at least one nucleic acid sequence containing a first mutation which inhibits the proper expression of a transgene, and at least one nucleic acid sequence containing a second mutation which abolishes the inhibition due to the first mutation.

The present invention also is directed to a method of treating a subject having a disease involving excessive cell proliferation, wherein the method comprises administering to the subject a cell proliferation inhibiting amount of the nucleic acid construct of the present invention. The diseases for which the nucleic acid constructs are particularly useful is in the treatment of tumors and cardiovascular diseases involving proliferation of cells in blood vessels.

The present invention is additionally directed to a pharmaceutical composition containing a cell proliferation inhibiting amount of the nucleic acid construct in a pharmaceutically acceptable carrier.

The present invention is also directed to a method of treating a subject having any one of the following medical conditions: autoimmune disease, allergies, inflammation, organ rejection, arthritis, infectious disease or neuron disease, wherein the method comprises administering to a subject a medical condition treating amount of the nucleic acid construct of the present invention.

The nucleic acid constructs disclosed in the figures are merely examples of preferred embodiments and are not meant to limit the invention to the specific components disclosed therein.

BRIEF DESCRIPTION OF THE DRAWINGS

FIGS. 5A and 5B depict the arrangement of the individual components in a further nucleic acid constructs in alternative schemes.

FIG. 6 depicts the arrangement of the individual components in a further nucleic acid construct.

DETAILED DESCRIPTION OF PREFERRED EMBODIMENTS

The present invention is directed to nucleic acid constructs for use in the regulated expression of transgenes in host cells containing at least one nucleic acid sequence containing a first mutation which inhibits the proper expression of the transgene, and at least one further nucleic acid sequence containing a second mutation which abolishes the inhibition due to the mutation in the first nucleic acid sequence(s).

These nucleotide sequences are under the control of identical or different promoter sequences, so that a transgene can only be expressed when all these promoter sequences are activated.

Preferably, the novel nucleic acid constructs comprise at least the following components, listed in a 5' to 3' end direction reading frame:

a first promoter or enhancer sequence (a) which activates the transcription of the transgene and which optionally contains a mutation which inhibits the function of the first promoter (a'), a transgene (b') encoding a pharmacologically active compound which optionally contains a mutation (b) which stops the transcription and/or the translation of the transgene or inhibits the function of the pharmacologically active compound, a second promoter or enhancer sequence (c) which activates the basal transcription of the component (d), and which optionally contains a mutation which inhibits the function of the second promoter, a gene for a tRNA (suppressor tRNA) or a regulatory protein (d) for abolishing the mutation in at least one of the promoters (a) or (c) or in the transgene (b).

Figure 1A:
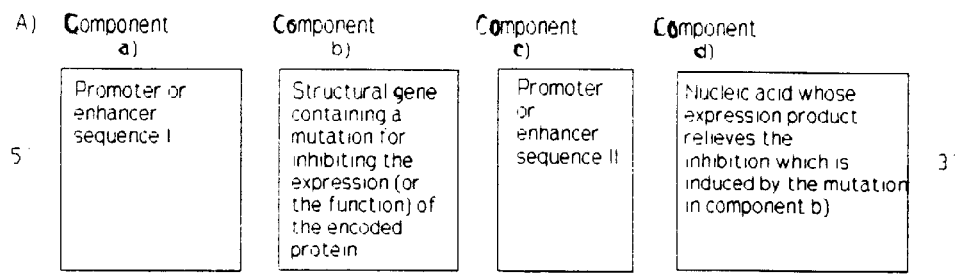
FIGS. 1A and 1B depict the arrangement of the individual components in a nucleic acid construct in alternative schemes.
Figure 1B:
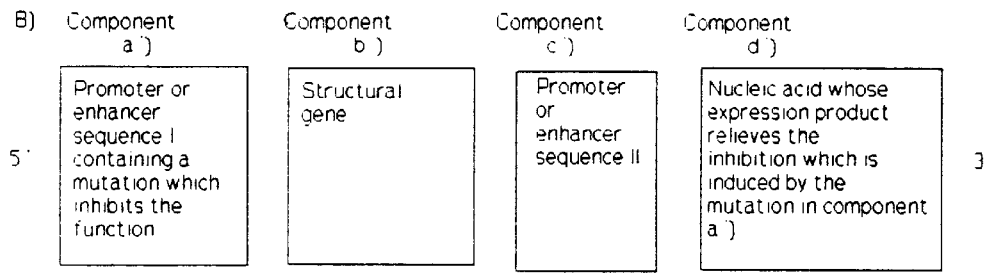

The arrangement of the individual components is depicted by way of example in FIGS. 1A and 1B (Schemes A and B). These figures show alternative embodiments of the nucleic acid constructs.

In the novel nucleic acid constructs of the present invention, the promoter or enhancer sequences of the components (a) or (c) can be identical or different and, furthermore, the components (c) and (d) can be located upstream or downstream of the components (a) and (b).

At least one strong promoter sequence or enhancer sequence, such as derived from CMV (EP-A-0173177) or SV40, or a tetracycline operator in combination with a corresponding repressor, or any other promoter sequence or enhancer sequence, which is known to the skilled person, is preferably used as the promoter sequence or enhancer sequence.

In a preferred embodiment, at least one promoter sequence or enhancer sequence in the novel nucleic acid constructs can be activated cell-specifically, metabolically (e.g. by hypoxia), virus-specifically or cell cycle-specifically.

Particular preference is given to the following promoter or enhancer sequences:

those promoter sequences or enhancer sequences which activate transcription cell-specifically in endothelial cells, smooth muscle cells, striated muscle cells, hematopoietic cells, lymphocytes, macrophages, glia cells or tumor cells; and/or promoter sequences or enhancer sequences of the HBV, HCV, HSV, HPV, CMV, EBV, HTLV or HIV viruses; and/or promoter sequences or enhancer sequences which can be metabolically activated, such as the hypoxia-inducible enhancer (Semenza et al., PNAS 88, 5680 (1991)) or promoter (Mc Burney et al., Nucleic Acids Res. 19, 5755 (1991); WO 95/21927); and/or promoters which can be activated cell cycle-specifically, such as the promoter of the cdc25C gene, of the cyclin A gene, of the cdc2 gene (Lucibello et al., EMBO J. 14, 132 (1995), Zwicker et al., EMBO J. 14, 4514 (1995), Zwicker et al., Nucl. Acids Res. 23, 2833 (1995)), of the B-myb gene (Lam et al., EMBO J. 12, 2705 (1993)), of the DHFR gene (Means et al., Mol. Cell Biol. 12, 1054 (1992)) and of the E2F-1 gene (Johnson et al., Genes Dev. 8, 1514 (1994), Hsiao et al., Genes Dev. 8, 15256 (1994)) or else sequences for binding transcription factors which appear or are activated during cell proliferation. Examples of these binding sequences are monomers or multimers of the nucleotide sequence termed the Myc E box (Blackwood and Eisenmann, Science 251, 1211 (1991)).

Further, promoters which can be activated by tetracycline, such as a tetracycline operator in combination with a corresponding repressor (Gossen et al., TIBS 18, 471 (1993), Dingermann et al. EMBO J. 11, 1487 (1992), Gossen et al., Science 268, 1766 (1995)) are also intended to be utilized within the scope of the present invention.

In another preferred embodiment, at least one promoter sequence or enhancer sequence in the novel nucleic acid constructs is a chimeric promoter. Within the meaning of this invention, a chimeric promoter is the combination of an upstream activator sequence, which can be activated cell-specifically, metabolically or virus-specifically, and a downstream promoter module. Preferably, the promoter module comprises a nucleotide sequence which contains a CDE-CHR element or an E2FBS-(Bmyb)-CHR element, and can thereby inhibit the activation of the upstream activator sequence in the G0 and G1 phases of the cell cycle (Lucibello et al., EMBO J. 14, 132 (1994), PCT/GB95/ 02000; Zwicker et al., EMBO J. 14, 4514 (1995); Zwicker et al., Science 271, 1595 (1996)).

In another preferred embodiment, at least one promoter sequence or enhancer sequence (component a) or c)) in the novel nucleic acid constructs is an activator-responsive promoter unit.

For its part, an activator-responsive promoter unit is composed of the following components:

one or more identical or different promoter or enhancer sequence(s) (e) which can be activated, for example, cell cycle-specifically, metabolically, cell-specifically or virus-specifically, or both cell cycle-specifically and metabolically, cell-specifically or virus-specifically (so-called chimeric promoters), one or more identical or different activator subunit(s) (f) which is/are, in each case, located downstream of the promoter or enhancer sequences and whose basal transcription is activated by these latter sequences, and an activator-responsive promoter (g) which is activated by the expression products of one or more activator subunit(s).

Figure 2:
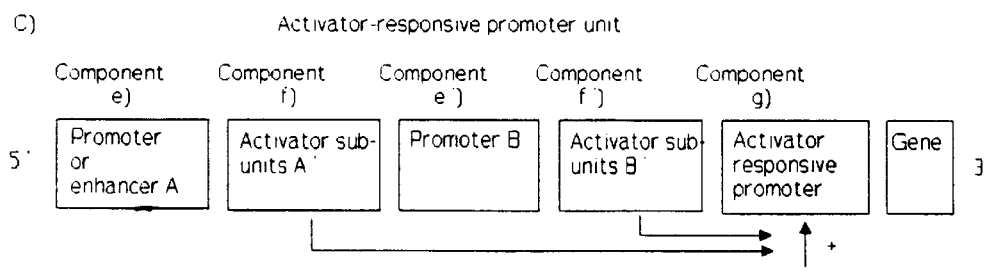
FIG. 2 depicts the arrangement of the individual components of an activator-responsive promoter unit. Horizontal arrows indicate that the expression products of the activator subunits (f) and (f') respectively interact with the activator responsive promoter, the interaction being activating (vertical arrow +).

The arrangement of the individual components of an activator-responsive promoter unit is depicted, by way of example, by Scheme C in FIG. 2.

Figure 3:
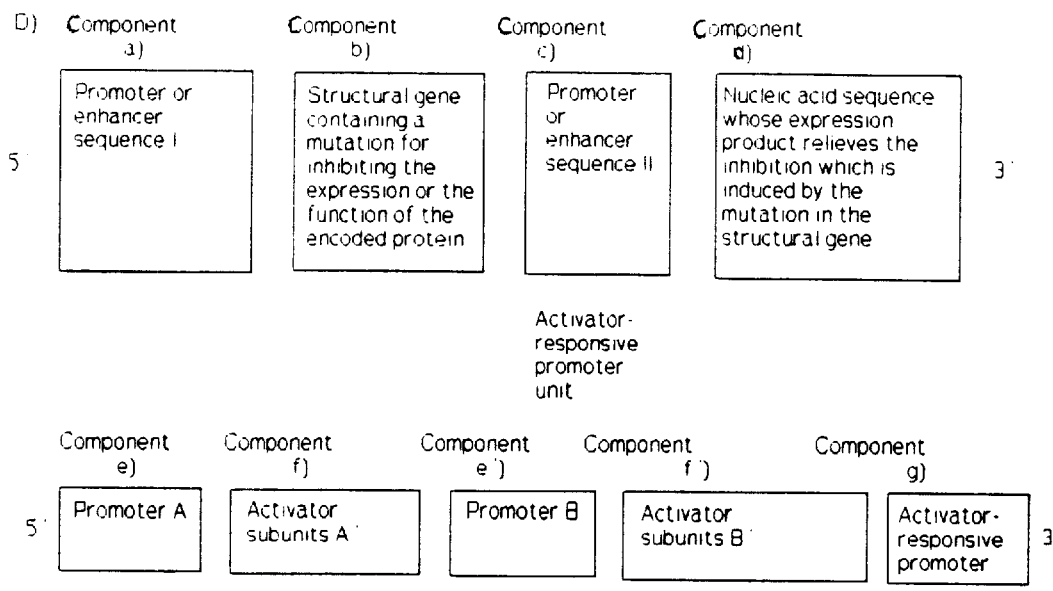
FIG. 3 depicts a preferred activator-responsive promoter unit in a nucleic acid construct.

The insertion of a preferred activator-responsive promoter unit into a novel nucleic acid construct is depicted, by way of example, by Scheme D in FIG. 3.

Figure 4:
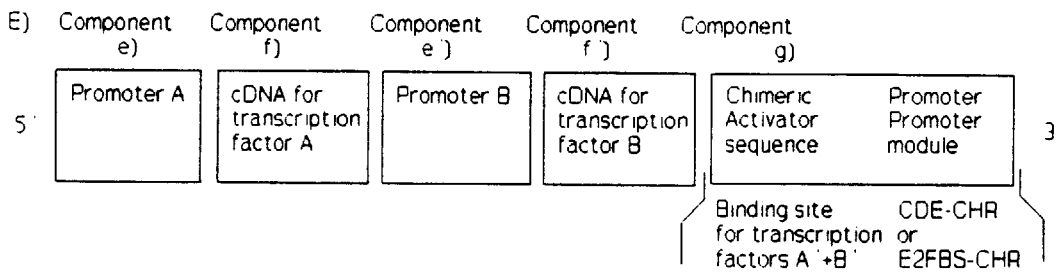
FIG. 4 depicts an activator-responsive promoter units utilizing chimeric promoter constructs.

In their simplest form, activator-responsive promoter units can, for example, be chimeric promoter constructs as depicted in Scheme E in FIG. 4.

In another embodiment, activator-responsive promoter units according to the invention can be sequences for binding chimeric transcription factors with are composed of DNA-binding domains, protein-protein interaction domains and transactivating domains.

Structural genes which are preferred as pharmacologically active compound are proteins and glycoproteins which are selected from the group consisting of cytokines, growth factors, receptors for cytokines or growth factors, antibodies or antibody fragments, fusion proteins composed of ligands (e.g. antibodies or antibody fragments) and cytokines or growth factors, proteins having an antiproliferative, apoptotic, cytostatic, or cytolytic effect, angiogenesis inhibitors, thrombosis-inducing proteins, coagulation inhibitors, proteins having a fibrinolytic effect, blood plasma proteins, complement-activating proteins, such as cobra venom factor, human C3b and modified C3b, bacterial proteins and antigens, bacterial and viral coat proteins, bacterial, parasitic and tumor antigens, proteins having an effect on the blood circulation, peptide hormones, enzymes, fusion proteins composed of a ligand and an active compound, antisense RNA, and ribozymes.

In conformity with the invention, the structural genes (transgene—component (b)) in one particular embodiment are provided with a mutation which prevents the expression of a functioning protein (or peptide).

This mutation can be the replacement of a nucleotide sequence for one or more amino acids such that, as a result of this replacement, the expressed protein is no longer capable of functioning (missense mutation), i.e. no longer produces any active compound or any functioning enzyme. In the case of a mutation of the structural gene (transgene—component (b)) of this nature, the component (d) is a nucleic acid sequence which encodes a tRNA which, on the one hand, binds, by its anticodon, to the mutation site of the mRNA of the structural gene (component (b)) and, on the other hand, carries an end group which takes up the correct amino acid for relieving the mutation in the transgene (suppressor tRNA).

In this context, those tRNAs which are normally only used rarely in mammalian cells should, in particular, be mutated into suppressor tRNAs, in order to minimize negative consequences for the general translation efficiency of the cell.

In another embodiment, the mutation in the structural gene is the introduction of one or more translation stop codons (nonsense mutations). In mRNA, the nucleotide sequences UAA, UGA and UAG are known to be translation stop codons. The corresponding DNA sequences for these stop codons are TAA, TGA and TAG/coding strand of the DNA. One of these stop codons is preferably inserted, as a mutation, into the DNA sequence of the structural gene (component (b)).

In the case of a mutation of the structural gene (component (b)) of this nature, the component (d) is a nucleic acid sequence which encodes a tRNA (suppressor tRNA) which, on the one hand, binds, by its anticodon, to the mutation, i.e. to the introduced stop codon of the mRNA of the structural gene (component (b)), and, on the other hand, carries an end group which takes up the correct amino acid which was encoded by the original DNA sequence at the site of the mutation. Nucleic acid sequences (b) of this nature have already been described for *E. coli*, yeast and plant cells (Dingermann et al., Mol. Cell Biol. 12, 4038 (1992), EMBO J. 11, 1487 (1992); Gossen et al. TIBS 18, 471 (1993); Gatz et al., Plant. J. 2, 397 (1992)). In conformity with the invention, tRNAs which are normally only used rarely in mammalian cells should be mutated into suppressor tRNAs in this case too.

Thus, the following combinations, for example, can be selected (Lewin Ed. Genes IV, Oxford University Press 1990, page 151):

TABLE 1

| Amino acid | Codon | Stop mutation (codon) | Suppressor tRNA (anticodon) | Amino acid bound to suppressor tRNA | Gene locus |
|---|---|---|---|---|---|
| Tyr | UAU | UAG | CUA | Tyr | sup F (su+3) |
| Tyr | UAC | UAA | UUA | Tyr | sup C (su+4) |
| Ser | UCG | UAG | CUA | Ser | sup D (su+1) |
| Gln | CAG | UAG | CUA | Gln | sup E (su+2) |
| Lys | AAA | UAA | UUA | Lys | sup G (su+5) |
| Lys | AAG | UAG | UUA | Lys | sup G (su+5) |
| Trp | UGG | UGA | UCA | Trp | sup U (su+7) |
| Trp |  | UGG | UCA | Trp | sup U (su+7) |

In another embodiment, the mutation in or on the structural gene can be a mutation of the TATA box of a promoter sequence (component (a)) which is located upstream of the 5' end of the structural gene (component (b)). The TATA box (TATAAA) is considered to be a central initiation site for the RNA polymerases II and III which are present in the cell nucleus. Transcription is initiated at the TATA box by the binding of the TATA box-binding protein (TBP), which is involved, in an essential manner, in the transcription of all the RNA polymerases (I, II, III) which are present in the cell nucleus. An example of a promoter which is strictly TATA box-dependent is the promoter for the U6 gene, which is transcribed by RNA polymerase III and whose gene product is involved, in an essential manner, in the splicing of mRNA.

In conformity with this invention, a promoter (component (a)) which is dependent on a mutated TATA box is located upstream of the 5' end of the structural gene (component (b)). An example of such a mutation can be TGTAAA. As a result of this mutation, the DNA-binding site of the normal TBP is no longer recognized and the structural gene (b) is no longer transcribed efficiently. In the case of a mutation of this nature, the component (d) is a nucleic acid sequence which encodes a comutated TBP. As a result of this comutation, the TBP binds to the mutated TATA box (e.g. to TGTAAA) in component (a) and consequently gives rise to efficient transcription of the structural gene (component (b)). Such comutations of the TBP gene have been described, for example, by Strubin and Struhl (Cell 68, 721 (1992)) and by Heard et al. (EMBO J. 12, 3519 (1993)).

In another preferred embodiment, a nuclear retention signal (NRS) (h) and, where appropriate, a nuclear export signal are added to the novel nucleic acid construct. The arrangement of the individual components in a novel nucleic acid construct is depicted in Schemes F) and G) in FIGS. 5A and 5B.

In another preferred embodiment, the nucleic acid constructs which are depicted in Schemes F) and G) are combined with each other. Combining in this way enables another promoter (promoter IV, component (e)) to be included. The arrangement of the individual components in this combination is depicted, by way of example, by Scheme H) in FIG. 6.

The nuclear retention signal is a nucleotide sequence which impedes the transport of a pre-messenger RNA which is linked to it through the nuclear membrane but which, on the other hand, constitutes a structure for binding an export protein termed a nuclear export factor. This nuclear export factor (NEF) mediates the transport of the NRS-containing premessenger or messenger RNA out of the cell nucleus into the cytoplasm. A premessenger or messenger RNA which contains the NRS is consequently secreted out of the cell nucleus by binding to the NEF (Fischer et al., Cell 82, 475 (1995)).

The NRS (component (h)) is preferably the retroviral rev-responsive element (RRE) sequence. In the case of HIV-1, this RRE is a sequence encompassing 243 nucleotides (nucleotides 7362–7595; Muesing et al., Nature 313, 450 (1985)) in the env gene (Malim et al., Nature 338, 254 (1989); Kjems et al., PNAS 88, 683 (1991)). However, within the meaning of the invention, the nuclear retention signal (NRS) can also be any homologous and/or functionally similar (analogous) nucleotide sequence, such as, for example, the RRE-equivalent element in the HBV virus (Huang et al., Mol Cell Biol. 13, 7476 (1993)).

In the novel nucleic acid constructs, the nuclear export factor (NEF, component (k)) is a nucleotide sequence which encodes a protein which binds to the mRNA of the NRS and mediates transport of the premessenger RNA or messenger RNA which contains an NRS out of the cell nucleus into the cytoplasm (or out of the cytoplasm into the cell nucleus). Within the context of the invention, use is made, in particular, of the rev gene which is derived from retroviruses, especially from the H[V-1 virus or HIV-2 virus (Daly et al., Nature 342, 816 (1989); Emerman et al., Cell 57, 1155 (1989); Felber et al., PNAS 86, 1495 (1989); Fischer et al., EMBO J. 13, 4105 (1994)).

The rev protein of the retroviral rev gene binds, by its N-terminal domain (Zapp et al., Nature 342, 714 (1989); Malim et al., Cell 65, 241(1991)) to the RRE in the pre-mRNA (Iwai et al., Nucl. Acids Res. 20, 6465 (1992)). The binding between the RRE and the rev protein enables nonspliced premessenger RNA, and also any other RNA which contains an RRE, to be transported out of the cell nucleus into the cytoplasm (Fischer et al., EMBO J. 13, 4105 (1994); Fischer et al., Cell 82, 475 (1995)) and consequently augments translation substantially.

Within the context of the invention, nucleotide sequences which encode proteins which are homologous, and functionally similar, to the HIV-1 rev protein (Bogerd et al., Cell 82, 485 (1995)), such as the visna maedi virus (VMV; Tiley et al., J. Virol. 65, 3877 (1991)) rev gene or the caprine arthritis encephalitis virus (CAEV; Tiley et al., J. Virol. 65, 3877 (1991)) rev gene, can also be used as NEF.

However, within the context of the invention, those genes can also be employed which encode proteins which, while possessing only slight homology, or no homology, with the rev protein, are functionally similar to the HIV-1 rev protein.

Examples of these genes are the HTLV-1 rex gene (Cullen, Microbiol. Rev. 56, 375 (1992)), the equine infectious anemia virus EIAV) rev gene and the feline immunodeficiency virus (HV) rev gene (Manusco et al., J. Virol. 68, 1988 (1994)).

In an alternative embodiment, the NEFs can also be nucleotide sequences for proteins which bring about secretion of RNA from the nucleus even without this RNA being retained in the nucleus by an NRS. Examples of such proteins are the transcription factor TFIIIA (Gaddat et al., Cell 60, 619 (1990); Drew et al., Gene 159, 215 (1995)) or the heterogeneous nuclear ribonucleoprotein A1 (hnRNPA1-Protein; Pinol-Roma et al., Nature 355, 730 (1992)).

In a broader sense, the nuclear transport proteins also include heat shock protein 70 (hsc70; Mandell et al., J. Cell Biol. 111, 1775 (1990)) and the protein kinase inhibitor CPKI (Fantozzi et al., J. Biol. Chem. 269, 2676 (1994), Wen et al., J. Biol. Chem. 269, 32214 (1994).

Features possessed in common by the NEF and its homologous and analogous proteins are a domain, which is situated towards the aminoterminus, for binding the monomeric protein to the RNA of the NRS (J. Virol 64, 881 (1990); Kjems et al., EMBO J. 11, 1119 (1992)) and a domain, which is for the most part leucine-rich (hnRNPA1 is an exception to this) and which is required for the NEF transport function (Wen et al., Cell 82, 463 (1995); Fischer et al., Cell 82, 475 (1995); Malim et al., J. Virol. 65, 4248 (1991); Venkatesh et al., Virol. 178, 327 (1990)).

The expression of the NEF gene (component (k)) can be under the control of a promoter sequence (component i)=promoter and enhancer sequence III) which is located upstream at the 5' end of the NEF gene.

One of the nucleic acid sequences as already described for promoter and enhancer sequences I and II (components (a) and (c)) can be selected as promoter and enhancer sequence III or IV in conformity with this invention (see Scheme H of FIG. 6)).

The nucleic acid constructs are preferably composed of DNA. The term "nucleic acid constructs" is understood to mean artificial nucleic acid structures which can be transcribed in the target cells. They are preferably inserted into a vector, with nonviral vectors, plasmid vectors or viral vectors being particularly preferred. These vectors are mixed with pharmaceutically acceptable carriers to produce pharmaceutical compositions for use in gene therapy. The pharmaceutically acceptable carriers are well known to persons skilled in the art, and the optimal dosage of vectors containing the nucleic acid construct can be readily determined using conventional techniques. The pharmaceutical composition is then administered locally to patients for the prophylaxis or therapy of a disease, or is injected or administered intravenously, intraarterially, into a body cavity, into an organ or subcutaneously. In the case of treating tumors, the pharmaceutical composition is injected injected directly into the tumors. However, other known delivery methods with appropriate carriers can be utilized, such as catheter based gene delivery.

The term "treatment" as it pertains to administering the vectors containing the nucleic acid constructs of the present invention to patients is understood to include administration to patients for the purpose of prophylaxis and amelioration of the disease. These vectors are particularly useful in diseases with excessive cell proliferation.

The novel nucleic acid constructs can be used to express a transgene (component b)) both cell-specifically or virus-specifically or under defined metabolic conditions or following exposure to tetracycline and also cell cycle-specifically, with the structural gene preferably being a gene which encodes a pharmacologically active compound or else an enzyme which cleaves an inactive precursor of a drug to form an active drug. The structural gene can be selected, such that this pharmacologically active compound, or this enzyme, is expressed together with a ligand as a fusion protein and this ligand binds to the surface of cells, e.g. proliferating endothelial cells or tumor cells.

The present invention also relates to yeast cells or mammalian cells which harbor a novel nucleic acid construct. In a particularly preferred embodiment, the nucleic acid constructs are introduced into cell lines which can then be used to express the transgene following transfection. These cells can consequently be used for preparing a pharmaceutical for patients and also be locally administered to, or injected into patients for the prophylaxis or treatment of a disease.

The novel nucleic acid constructs do not occur in this form in nature, i.e. the transgene or structural gene for the active compound or for an enzyme or for a ligand/enzyme fusion protein is not naturally mutated and is not naturally combined with a nucleic acid sequence which relieves this mutation; furthermore, it is also not naturally combined with the nuclear retention signal (NRS) and the two sequences are not naturally linked to the promoter I(a) and the promoter II(c), and this combination is in turn not naturally combined with the nucleotide sequence which is composed of the promoter III and the nuclear export factor (NEF).

Promoters I, II, III and IV, and the structural gene for the active compound (or for the enzyme), of the novel nucleic acid constructs are selected as a function of the application.

Depending on the planned use of the nucleic acid constructs, the following embodiments can be selected:

1. The Therapy of Tumors and Chronic Inflammations by Inhibiting the Proliferating Endothelium 1.1.a) Selection of the Promoters or Activator Sequences which are Activated in Endothelial Cells Within the context of this invention, the preferred promoters or activator sequences composed of promoters or enhancers include those gene-regulatory sequences and/or elements for genes which encode proteins which can be detected, in particular, in endothelial cells (or else in cells which are in the immediate vicinity of proliferating endothelial cells).

Some of these proteins have been described by Borrows et al. (Pharmac. Ther. 64, 155 (1994)) and Plate et al. (Brain Pathol. 4, 207 (1994)). Particular examples of these endothelial cell-specific proteins are:

Brain-specific, endothelial glucose-1-transporter
  The promoter sequence was described by Murakami et al. (J. Biol. Chem. 267, 9300 (1992)).
Endoglin
  A part of the promoter sequence was described by Bellon et al. (Eur. J., Immunol. 23, 2340 (1993)) and Ge et al. (Gene 138, 201 (1994)).
VEGF receptors
Two different receptors are recognized (Plate et al., Int. J. Cancer 59, 520 (1994)):
  VEGF receptor-1 (flt-1) (de Vries et al., Science 255, 989 (1992); Wakiya et al. J. Vascul. Res. 33, 105 (1996)) and the
  VEGF receptor-2 (flk-1, KDR)
  (Terman et al., BBRC 187, 1579 (1992)).
    Both the receptors are to be found almost exclusively on endothelial cells (Senger et al., Cancer Metast. Rev. 12, 303 (1993)).
Other endothelial cell-specific receptor tyrosine kinases tie-1 or tie-2
  (Partanen et al., Mol. Cell. Biol. 12, 1698 (1992), Schnürch and Risau, Development 119, 957 (1993), Dumont et al., Oncogene 7, 1471 (1992)).
B61 receptor (Eck receptor)
  (Bartley et al., Nature 368, 558 (1994), Pandey et al., Science 268, 567 (1995), van der Geer et al., Ann. Rev. Cell. Biol. 10, 251 (1994)).
B61
The B61 molecule is the ligand for the B61 receptor.
  (Holzman et al., J. Am. Soc. Nephrol. 4, 466 (1993), Bartley et al., Nature 368, 558 (1994)).
Endothelin, especially
  Endothelin B
    The promoter sequence was described by Benatti et al., J. Clin. Invest. 91, 1149 (1993).
  Endothelin-1
    The promoter sequence was described by Wilson et al., Mol. Cell. Biol. 10, 4654 (1990).
Endothelin receptors, in particular the endothelin B receptor
  (Webb et al., Mol. Pharmacol. 47, 730 (1995), Haendler et al. J. Cardiovasc. Pharm. 20, 1 (1992)).
Mannose-6-phosphate receptors
  The promoter sequences have been described by Ludwig et al. (Gene 142, 311 (19949), Oshima et al., (J. Biol. Chem. 263, 2553 (1988)) and Pohlmann et al. (PNAS USA 84, 5575 (1987)).
von Willebrand factor
  The promoter sequence was described by Jahroudi and Lynch (Mol. Cell. Biol. 14, 999 (1994)), Ferreira et al. (Biochem. J. 293, 641 (1993)) and Aird et al. (PNAS USA 92, 4567 (1995)).
IL-1α, IL-1β
  The promoter sequences were described by Hangen et al., Mol. Carcinog. 2, 68 (1986), Turner et al., J. Immunol. 143, 3556 (1989), Fenton et al., J. Immunol. 138, 3972 (1987), Bensi et al., Cell Growth Diff. 1, 491 (1990), Hiscott et al., Mol. Cell. Biol. 13, 6231 (1993) and Mori et al., Blood 84, 1688 (1994).
IL-1 receptor
  The promoter sequence was described by Ye et al., PNAS USA 90, 2295 (1993). Vascular cell adhesion molecule (VCAM-1)
  The promoter sequence of VCAM-1 was described by Neish et al., Mol. Cell. Biol. 15, 2558 (1995), Ahmad et al., J. Biol. Chem. 270, 8976 (1995), Neish et al., J. Exp. Med. 176, 1583 (1992), Jademarco et al., J. Biol. Chem. 267, 16323 (1992), and Cybulsky et al., PNAS USA 88, 7859 (1991).
Synthetic activator sequence
  As an alternative to natural, endothelium-specific promoters, use can also be made of synthetic activator sequences which comprise oligomerized binding sites for transcription factors which are preferentially or selectively active in endothelial cells. An example of such a transcription factor is the transcription factor GATA-2, whose binding site in the endothelium-1 gene is 5'-TTATCT-3' (Lee et al., Biol. Chem. 266, 16188 (1991), Dorfmann et al., J. Biol. Chem. 267, 1279 (1992) and Wilson et al., Mol. Cell Biol. 10, 4854 (1990)).

1.1.b) Selection of the Promoters or Activator Sequences Which are Activated in Cells in the Vicinity of Activated Endothelial Cells When endothelial cells are proliferating, neighboring cells become accessible, by way of opening tight junctions, to macromolecules derived from the blood. As a result of the functional and anatomical interrelationships, the cells which neighbor activated endothelial cells are target cells within the meaning of this invention.

VEGF
  The gene-regulatory sequences for the VEGF gene are the promoter sequence of the VEGF gene (5' flanking region)
    (Michenko et al., Cell. Mol. Biol. Res. 40, 35 (1994), Tischer et al., J. Biol. Chem. 266, 11947 (1991)) or the enhancer sequence of the VEGF gene (3' flanking region)
(Michenko et al:, Cell Mol. Biol. Res. 40, 35 (1994)) or
the c-Src gene
(Mukhopadhyay et al., Nature 375, 577 (1995), Bonham et al., Oncogene 8, 1973 (1993), Parker et al., Mol. Cell. Biol. 5, 831 (1985), Anderson et al., Mol. Cell. Biol. 5, 112 (1985)) or
the v-Src gene
(Mukhodpadhyay et al., Nature 375, 577 (1995), Anderson et al., Mol. Cell. Biol. 5, 112 (1985), Gibbs et al., J. Virol. 53, 19 (1985)).

Steroid hormone receptors and their promoter elements (Truss and Beato, Endocr. Rev. 14,;459 (1993)), in particular the
mouse mammary tumor virus promoter
The cDNA sequence of the promoter region of the long terminal repeat region of MMTV has been described by Chalepakis et al., Cell 53, 371 (1988) and Truss and Beato (Endocr. Rev. 14, 459 (1993).

1.2. Structural Genes for Antitumoral (or Antiinflammatory) Substances 1.2.a) Inhibitors of Proliferation Within the meaning of this invention, an antitumoral or antiinflammatory substance is to be understood as being the DNA sequence of a protein which inhibits the proliferation of endothelial cells. Examples of these DNA sequences are the DNA sequences for:

the retinoblastoma protein (pRb/p110) or for its analogs p107 and 120 the p53 protein the p21 (WAF-1) protein the p16 protein other CdK inhibitors the GADD45 protein the bak protein.

In order to prevent rapid intracellular inactivation of these cell cycle inhibitors, use is preferably to be made of those genes which exhibit mutations for the inactivation sites of the expressed proteins without the function of these proteins thereby being impaired.

The retinoblastoma protein (pRb) and the related p107 ad p130 proteins are inactivated by phosphorylation. Preference is therefore given to using a pRb/p110, p107 or p130 cDNA sequence which is point-mutated such that the phosphorylation sites of the encoded protein are replaced with amino acids which cannot be phosphorylated.

1.2.b) Coagulation-inducing Factors and Angiogenesis Inhibitors

An antitumoral or antiinflammatory substance is also to be understood as being the DNA sequence for a protein which induces coagulation and/or inhibits angiogenesis. Examples of these proteins are:

Tissue factor (TF) and coagulation-active fragments thereof
(Morrissey et al., Cell 50, 129 (1987), Scarpati et al., Biochem. 26, 5234 (1987), Spicer et al., PNAS USA 84, 5148 (1987), Rehemtulla et al., Thromb. Heamost. 65, 521 (1991))

Plasminogen activator inhibitor-1 (PAI-1)

PAI-2

PAI-3

Angiostatin and similar anti-angiogenic peptides
(O'Reilly et al., Nature Med. 2, 689 (1996); Folkman et al., New Engl. J. Med. 26, 1757 (1995))

Interferons
IFNα
IFNβ
IFNγ

Thrombospondin

TNFα

Platelet factor 4

IL-12

TIMP-1

TIMP-2

TIMP-3

Leukemia inhibitory factor (LIF)

1.2.c) Cytostatic and Cytotoxic Proteins

However, an antitumoral or antiinflammatory substance is also to be understood as being a DNA sequence for a protein which, directly or indirectly, exhibits a cytostatic effect on tumors. These proteins include, in particular:

Antibodies and antibody cleavage products

Perforin

Granzyme

IL-2

IL-4

IL-12

Interferons, for example
IFNα
IFNβ
IFNγ

TNF
TNFα
TNFβ

Oncostatin M

Sphingomyelinase (Jarvis et al. PNAS-USA 91, 73 (1994))

Magainin and magainin derivatives
(Cruciani et al. PNAS 88, 3792 (1991); Jacob et al., Ciba Found. Symp. 186, 197 (1994); Peck-Miller et al., Cancer Chemother. Pharmac. 32, 109 (1993)).

1.2.d) Inflammation Inducers

An antitumoral substance is also to be understood as being the DNA sequence for a protein which, in addition to the antitumoral effect, may also stimulate inflammations and thereby contribute to the elimination of tumor cells. Particular examples of these proteins are:

RANTES (MCP-2)

Monocyte chemotactic and activating factor (MCAF)

IL-8

Macrophage inflammatory protein-1 (MIP-1α and β)

Neutrophil activating protein-2 (NAP-2)

IIL-3

IL-4

IIL-5

Human leukemia inhibitory factor (LIF)

L-7

IL-13

GM-CSF

G-CSF

M-CSF

Cobra venom factor (CVF) or part sequences of CVF, which correspond functionally to human complement factor C3b, i.e. which are able to bind to complement factor B and, after cleavage with factor D, constitute a C3 convertase. The DNA sequence for CVF and its part sequences have been published by Frikinger et al., Proc. Natl. Acad. Sci. USA 91, 12775 (1994).

Human complement factor C3 and its part sequence C3b. The DNA sequence for C3 and its part sequences have been published by De Bruijn et al., Proc. Natl. Acad. Sci. USA 82, 708 (1985).

Cleavage products of human complement factor C3 which resemble CVF functionally and structurally. Cleavage products of this nature have been described by O'Keefe et al., J. Biol. Chem. 263, 12690 (1988).

Bacterial proteins which activate complement or trigger inflammations, such as *Salmonella typhimurium porins* (Galdiero et al., Infection and Immunity 46, 55 (1994)), *Staphylococcus aureus* clumping factors (Espersen Acta Path. Microb. Et Imm. Scandin. Sect C 93, 59 (1985)), modulins, particularly those of Gram-negative bacteria (Henderson et al., Inflam. Res. 44, 187 (1995)), major outer membrane protein from legionellas (Bellinger-Kawahara et al., J. Exp. Med. 172, 1201 (1990)) or from *Haemophilus influenzae* type B (Hetherington et al., Infection and Immunity 60, 19 (1992)) or from klebsiellas (Alberti et al., Infection and Immunity 61, 852 (1992)), or M molecules from group G streptococci (Campo et al., J. Infect. Dis. 171, 601 (1995)).

DNA sequences for fusion proteins which are formed between the listed cytokines or growth factors, on the one hand, and ligands for receptors on the cell membrane (such as an antibody which is specific for endothelial cells or tumor cells, or the Fc moiety of human immunoglobulin), on the other hand, can also be used as active substances within the context of the invention. DNA sequences of this nature, and their preparation, have been described, for example, in EPA 0464 633 A1.

1.2.e) Enzymes for Activating Precursors of Cytostatic Agents

However, an antitumoral or antiinflammatory substance is also to be understood as being the DNA sequence for an enzyme which is able to convert precursors of an antitumoral active compound into an antitumoral active compound.

Enzymes of this nature, which cleave inactive precursor substances (prodrugs) and thereby form active cytostatic agents (drugs), and the prodrugs and drugs which are in each case relevant, have already been reviewed by Deonarain et al. (Br. J. Cancer 70, 786 (1994)), by Mullen, Pharmac. Ther. 63, 199 (1994) and by Harris et al. (Gene Ther. 1, 170 (1994)).

For example, the DNA sequence of one of the following enzymes is to be used:

Herpes simplex virus thymidine kinase (Garapin et al., PNAS USA 76, 3755 (1979), Vile et al., Cancer Res. 53, 3860 (1993), Wagner et al., PNAS USA 78, 1441 (1981), Moelten et al., Cancer Res. 46, 5276 (1986), J. Natl. Cancer Inst. 82, 297 (1990)).

Varicella zoster virus thymidine kinase (Huber et al., PNAS USA 88, 8039 (1991), Snoeck, Int. J. Antimicrob. Agents 4, 211 (1994)).

Bacterial nitroreductase
(Michael et al., FEMS Microbiol. Letters 125, 195 (1994), Bryant et al., J. Biol. Chem. 266, 4126 (1991), Watanabe et al., Nucleic Acids Res. 18, 1059 (1990)).

Bacterial β-glucuronidase
(Jefferson et al., PNAS USA 83, 8447 (1986)).

Plant β-glucuronidase from Secale cereale
(Schulz et al., Phytochemistry 26, 933 (1987)).

Human β-glucuronidase
(Bosslet et al., Br. J. Cancer 65, 234 (1992), Oshima et al., PNAS USA 84, 685 (1987))
human carboxypeptidase (CB), e.g.
mast cell CB-A
(Reynolds et al., J. Clin. Invest. 89, 273 (1992)).
pancreatic CB-B
(Yamamoto et al., J. Biol. Chem. 267, 2575 (1992), Catasus et al., J. Biol. Chem. 270, 6651 (1995)).
bacterial carboxypeptidase
(Hamilton et al., J. Bacteriol. 174, 1626 (1992), Osterman et al., J. Protein Chem. 11, 561 (1992)).

Bacterial β-lactamase
(Rodrigues et al., Cancer Res. 55, 63 (1995), Hussain et al., J. Bacteriol. 164, 223 (1985), Coque et al., EMBO J. 12, 631 (1993)).

Bacterial cytosine deaminase
(Mullen et al., PNAS USA 89, 33 (1992), Austin et al., Mol. Pharmac. 43, 380 (1993), Danielson et al., Mol. Microbiol. 6, 1335 (1992)).

Human catalase or peroxidase
(Ezurum et al., Nucl. Acids Res. 21, 1607 (1993)).

Phosphatase, in particular
human alkaline phosphatase
(Gum et al., Cancer Res. 50, 1085 (1990)).
human acid prostate phosphatase
(Sharieff et al., Am. J. Hum. Gen. 49, 412 (1991), Song et al., Gene 129, 291 (1993), Tailor et al., Nucl. Acids Res. 18, 4928 (1990)).
Type 5 acid phosphatase
Gene 130, 201 (1993)).

Oxidase, in particular
human lysyloxidase
(Kimi et al., J. Biol. Chem. 270, 7176 (1995))
human acid D-aminooxidase
(Fukui et al., J. Biol. Chem. 267, 18631 (1992))

Peroxidase, in particular
human glutathione peroxidase
(Chada et al., Genomics 6, 268 (1990), Ishida et al., Nucl. Acids Res. 15, 10051 (1987)).
human eosinophil peroxidase
(Ten et al., J. Exp. Med. 169, 1757 (1989), Sahamaki et al., J. Biol. Chem. 264, 16828 (1989)).
human thyroid peroxidase
(Kimura, PNAS USA 84, 5555 (1987)).

Galactosidase

In order to facilitate secretion of the listed enzymes, the homologous signal sequence which is in each case contained in the DNA sequence can be replaced with a heterologous signal sequence which improves extracellular secretion.

Thus, the signal sequence for β-glucuronidase (DNA position $\leq 27$ to 93; Oshima et al., PNAS 84, 685 (1987)) can, for example, be replaced with the signal sequence for immunoglobulin (DNA position $\leq 63$ to $\geq 107$; Riechmann et al., Nature 332, 323 (1988)) or by the signal sequence for CEA (DNA position $\leq 33$ to $\geq 134$; Schrewe et al., Mol. Cell. Biol. 10, 2738 (1990), Berling et al., Cancer Res. 50, 6534 (1990)) or with the signal sequence for human respiratory syncytial virus glycoprotein (cDNA for amino acids <38 to $\geq 50$ or 48 to 65; Lichtenstein et al., J. General Virol. 77, 109 (1996)).

In addition, preference is to be given to selecting DNAs for those enzymes which, as a result of point mutation, are stored to only a slight extent in lysosomes and are secreted to an increased extent. Point mutations of this nature have been described, for example, for β-glucuronidase (Shiplex et al., J. Biol. Chem. 268, 12193 (1993)).

A sequence for a transmembrane domain can be introduced, alternatively, or in addition, to the signal sequence, in order to anchor the enzyme in the cell membrane of the enzyme-forming cell.

Thus, the transmembrane sequence of human macrophage colony-stimulating factor (DNA position ≦1485 to ≧1554; Cosman et al., Behring Inst. Mitt. 83, 15 (1988)) or the DNA sequence for the signal and transmembrane region of human respiratory syncytial virus (RSV) glycoprotein G (amino acids 1 to 63 or their part sequences, amino acids 38 to 63; Vijaya et al., Mol. Cell Biol. 8, 1709 (1988), Lichtenstein et al., J. General Virol. 77, 109 (1996)) or the DNA sequence for the signal and transmembrane region of influenza virus neuraminidase (amino acids 7 to 35 or the part sequence amino acids 7 to 27; Brown et al., J. Virol. 62, 3824 (1988)) can be inserted between the DNA sequence for the promoter and the DNA sequence for the enzyme (e.g. the β-glucuronidase).

In order to amplify translation, the nucleotide sequence GCCACC or GCCGCC can be inserted at the 3' end of the promoter and directly prior to the 5' end of the start signal (ATG) of the signal or transmembrane sequence (Kozak, J. Cell. Biol. 108, 299 (1989)).

However, the nucleotide sequence for a glycophospholipid anchor can also be inserted in order to anchor the enzyme in the cell membrane of the enzyme-forming cells.

A glycophospholipid anchor is inserted at the 3' end of the nucleotide sequence for the enzyme; this insertion can be in addition to the insertion of a signal sequence.

Glycophospholipid anchors have been described, for example, for CEA (DNA position ≦893 to ≧1079; Berling a]., Cancer Res. 50, 6534 (1990)), for N-CAM (Cunningham et al., Science 236, 799 (1987)) and for other membrane proteins such as Thy-i (Clissold, Biochem. J. 281, 129 (1992)) or CD16 (Selvaray et al., Nature 333, 565 (1988)).

Ferguson et al. (Ann. Rev. Biochem. 57, 285 (1988)) have published a review of glycophospholipid-anchored membrane proteins.

Another option for anchoring enzymes to the cell membrane in conformity with the present invention is the use of a DNA sequence for a ligand-enzyme fusion protein. The specificity of the ligand of this fusion protein is directed against a membrane structure which is present on the cell membrane of proliferating endothelial cells or of tumor cells.

The ligands which bind to the surface of proliferating endothelial cells include, for example, antibodies or antibody fragments which are directed against membrane structures of endothelial cells, as have been described, for example, by Burrows et al. (Pharmac. Ther. 64, 155 (1994)), Hughes et al. (Cancer Res. 49, 6214 81989)) and Maruyama et al. (PNAS USA 87, 5744, 1990)). They include, in particular, antibodies against the VEGF receptors.

The murine monoclonal antibodies are preferably to be employed in humanized form. The humanization is effected in the manner described by Winter et al. (Nature 349, 293 (1991)) and Hoogenbooms et al. (Rev. Tr. Transfus. Hemobiol. 36, 19 (1993)). Antibody fragments are prepared in accordance with the state of the art, for example in the manner described by Winter et al. (Nature 349, 293 (1991)), Hoogenboom et al. (Ref. Tr. Transfus. Hemobiol. 36, 19 (1993); Girol. Mol. Immunol. 28, 1379 (1991)) or Huston et al. (Intern. Rev. Immunol. 10, 195 (1993)).

The ligands furthermore include all active compounds which bind to membrane structures or membrane receptors on endothelial cells. These active compounds include, for example, substances which contain terminal mannose, and, furthermore, IL-1 or growth factors or their fragments, or part sequences thereof, which bind to receptors which are expressed by endothelial cells, such as PDGF, bFGF, VEGF, TGFβ (Pusztain et al., J. Pathol. 169, 191 (1993)) or kinin and derivatives or analogs of kinin. They furthermore include adhesion molecules which bind to activated and/or proliferating endothelial cells. Adhesion molecules of this nature, such as sLex, LFA-1, MAC-1, LeCAM-1, VLA-1, VLA-4 or vitronectin and derivatives or analogs of vitronectin, have already been described (reviews in Augustin-Voss et al., J. Cell. Biol. 119, 483 (1992), Pauli et al., Cancer Metast. Rev. 9, 175 (1990), Honn et al., Cancer Metast. Rev. 11, 353 (1992); Varner et al., Cell Adhesion and Commun. 3, 367 (1995)).

However, the ligands also include antibodies or their fragments which are directed against tumor-specific or tumor-associated antigens on the tumor cell membrane.

Examples of antigens of this nature, and the relevant antibodies, are given in Sedlacek et al., Contrib. Oncol. 32 (1988) and Contrib. Oncol. 43 (1992). Antibody-enzyme fusion proteins have been described, for example, by Bosslet et al., Br. J. Cancer 65, 234 (1992). In order to facilitate secretion of the ligand/enzyme fusion proteins which have been cited, the homologous signal sequence which is in each case contained in the DNA sequence for the enzyme can, as already described, be replaced with a heterologous signal sequence which improves extracellular secretion.

1.3. Combination of Several Antitumoral or Antiinflammatory Substances

Figure 7:
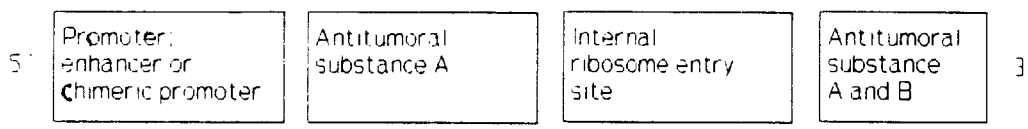
FIG. 7 depicts the arrangement of the individual components for several identical antitumoral or antiinflammatory substances (A,A) or different antitumoral substances (A,B) in a further nucleic acid construct.

The invention also relates to nucleic acid constructs which contain a combination of the DNA sequences for several identical antitumoral or antiinflammatory substances (A,A) or different antitumoral substances (A,B). For the purpose of expressing two DNA sequences, the cDNA of an internal ribosome entry site (IRES) is preferably intercalated as a regulatory element (see FIG. 7).

IRES of this nature have been described, for example, by Mountford and Smith (TIG 11, 179 (1995), Kaufman et al., Nucl. Acids Res. 19, 4485 (1991), Morgan et al., Nucl. Acids Res. 20, 1293 (1992), Dirks et al., Gene 128, 247 (1993), Pelletier und Sonenberg, Nature 334, 320 (1988) and Sugitomo et al., BioTechn. 12, 694 (1994).

Thus, the cDNA of the IRES sequence of poliovirus (position ≦140 to ≧630 of the 5' UTR; Pelletier and Sonenberg, Nature 334, 320 (1988)) can be used to link the DNA of the antiinflammatory substance A (at the 3' end) and the DNA of the antiinflammatory substance B (at the 5' terminus).

Depending on the combination, an active compound of this nature has an additive (A+A, A+B1) or synergistic effect within the context of the invention.

2. Active Compound for Relieving the Deficient Formation of Blood Cells 2.1. Selection of the Promoters or Activator Sequences for Hematopoietic Cells In the context of the present invention, a gene-regulatory sequence, or an element of a gene, which encodes a protein which is expressed particularly strongly or selectively in hematopoietic cells is preferably used as the promoter or activator sequence composed of promoters or enhancers. These gene-regulatory sequences include promoter sequences for genes for a cytokine, or its receptor, whose expression in the immature hematopoietic cells (or in neighboring cells, such as the stroma) takes place before that of the subsequent cytokine which is desired as an active substance and which exerts an effect on the hematopoietic cells. Examples of cytokines of this nature which exert an effect on immature hematopoietic cells are:

Stem cell factor

IL-1

IL-3

I6

GM-CSF 2.2. Selection of the Structural Genes for Active Substances for Hematopoietic Cells In the context of the invention, an active substance is to be understood as being a DNA sequence whose expressed protein brings about proliferation and/or differentiation of blood cells.

3. Active Compound for the Therapy of Autoimmune Diseases, Allergies and Inflammations, and for Preventing Organ Rejections 3.1. Selection of Promoters or Activator Sequences for, Inter Alia, Autoimmune Diseases Gene-regulatory sequences of the genes for those proteins which are formed to an increased extent in macrophages and/or lymphocytes during the immune reaction are to be used as promoters or activator sequences composed of promoters or enhancers. Examples of proteins of this nature are:

IL-1

1β

IL-1 receptor

IL-2

IL-2 receptor

IL-3

IL-3 receptor

IFNγ

IL-4

IL-4 receptor

IL-5

IL-6

LIF

IL-7

IL-l

IL-12

IL-13

GM-CSF

GM-CSF receptor

Integrin beta 2 proteins 3.2. Selection of the Genes for Active Substances for, Inter Alia, Auto-immune Diseases Within the context of the invention, the active substance is the DNA sequence coding for an antibody, an antibody fragment, a cytokine, a chemokine, a growth factor or one of its inhibitors, for a blood plasma protein, for a ribozyme which is catalytic for the transcription product of one of the DNA sequences or for the transcription product of a gene which encodes a cell cycle control protein or a DNA sequence for an antibody or for an enzyme. The selection of the active substance depends on the basic disease to be treated and on the chosen promoter sequence.

4. Active Compound for Treating Arthritis 4.1. Selection of the Promoters or the Activator Sequences for Arthritis Within the context of the invention, promoters, activator sequences composed of promoters or enhancers or gene-regulatory sequences are to be understood as being preferred which are associated with those genes with which transcription factors interact which are formed or are active in synovial cells and inflammatory cells. Within the context of this invention, the preferred promoter sequences include gene-regulatory sequences or elements from genes which encode proteins which are expressed, in particular, in synovial cells and inflammatory cells.

4.2. Selection of the Structural Genes for Active Substances for Arthritis

In the context of the invention, an active substance is to be understood as being a DNA sequence whose expressed protein directly or indirectly inhibits inflammation in a joint, for example, and/or promotes reconstitution of the extracellular matrix (cartilage, connective tissue) in the joint.

5. Preparation of an Active Compound Against Infective Agents

The active compound can be prepared in two forms which are fundamentally different:

for the therapy of viral infections and parasite invasions, or else for the prophylaxis of infectious diseases due to viruses, bacteria or parasites.

Vaccines are used for the prophylaxis of infectious diseases. However, the possibilities for preparing effective vaccines in the conventional way are limited (Brown, Int. J. Technol. Assessm. Health Care 10, 161 (1994)), Ellis, Adv. Exp. Med. Biol. 327, 263 (1992)), Arnon et al., FASEB J. 6, 3265 (1992)).

The technology of the DNA vaccines was therefore developed. However, these DNA vaccines raise questions with regard to the degree of efficacy, safety and side effects (Fynan et al., Int. J. Immunopharm. 17, 79 (1995), Donnelly et al., Immunol. 2, 20 (1994)).

Within the context of this invention, active compounds for the prophylaxis of infectious diseases are, on account of their cell specificity and cell cycle regulation, notable for a high degree of safety.

5.1. Selection of the Promoters or Activator Sequences 5.1.a) For the Therapy of Infectious Diseases Promoter sequences of cell genes whose activity is, in particular, altered by infections with bacteria or parasites are to be selected as activator sequences, or promoter sequences are to be selected which are derived from those viruses which transform the cells they have infected and stimulate these cells to proliferate.

Examples of these viruses are HBV, HCV, HSV, HPV, HIV, EBV and HTLV.

5.2. Selection of the Structural Genes for Active Substances 5.2.a) For the Therapy of Infectious Diseases The DNA for a protein which exhibits cytostatic, cytotoxic, antibacterial or antiviral effects is to be selected as the active substance. Examples of cytotoxic or cytostatic proteins have already been cited above. An antibody, or antibody fragments, may be mentioned as examples of antibacterial or antiviral proteins. When an enzyme is selected, the precursor of an antiviral cytotoxic or antiparasitic substance which can be cleaved by this enzyme has to be administered subsequently.

Active substances for antiviral proteins within the context of this invention are, furthermore, cytokines and growth factors which exhibit antiviral activity. These include, for example the DNA sequences for the following active substances:

IFNα
IFNβ
TNFγ
TNFβ
TNFα
IL-1
TGFβ

However, DNA sequences for fusion proteins which are formed between the listed cytokines, growth factors or the extracellular moiety of the receptors, on the one hand, and a ligand, on the other hand, can also be used as active substances within the context of the invention; for example, fusion proteins containing the Fc moeity of human immunoglobulin have been described in EPA 0464 633 A1.

Genes for ribozymes which digest the mRNA of genes for cell cycle control proteins or the mRNA of viruses are also regarded as being active substances. Ribozymes which are catalytic for HIV have been reviewed, for example by Christoffersen et al., J. Med. Chem. 38, 2033 (1995).

Furthermore, an active substance within the context of this invention is the DNA sequence for an antibody having a specificity which inactivates the relevant virus, or its $V_H$- and $V_L$-containing fragments, or its $V_H$ and $V_L$ fragments which are connected by way of a linker, which fragments are prepared, for example, in accordance with the methodology described by Marasco et al. (Proc. Natl. Acad. Sci. USA 90, 7889 (1993)). Examples of antibodies having a specificity of this nature against viruses are given in Section 5.2.b).

5.2.b) For the Prophylaxis of Infectious Diseases

The active substance to be selected is the DNA for either an antibody or an antibody fragment which is specific for the infective agent, or the DNA for a protein which is formed by the infective agent and which leads, by means of triggering an immune reaction, i.e. due to antibody binding and/or due to cytotoxic T lymphocytes, to the neutralization and/or destruction of the agent. So-called neutralization antigens of this nature are already employed as vaccine antigens (see review in Ellis, Adv. Exp. Med. Biol. 327, 263 (1992)). Examples of DNA sequences which encode neutralization antigens can be obtained from the following publications:

Influenza A virus antigen
(Ulmer et al., Science 259, 1745 (1993), Robinson et al., Vaccine 11, 957 (1993), Fynan et al., Int. J. Immunopharmac. 17, 79 (1995))

HIV antigens
(Wang et al., PNAS USA 90, 4156 (1993))

Rabies virus antigen
(Donnelly et al., Immunol. 2/1, 20 (1994))

HSV (herpes simplex virus) antigen
(Fleckenstein et al., Nature 274, 57 (1978))

RSV (respiratory syncytial virus) antigen
(Du et al., Bio/Tech. 12, 813 (1994), Hall, Science 265, 1393 (1993))

Parainfluenza virus antigen
(Du et al., Bio/Techn. 12, 813 (1994))

Rotavirus antigen
(Albert et al., J. Clin. Microbiol. 25, 183 (1987), Anderson et al., J. Infect. Dis. 153, 823 (1986), Battaglia et al., J. Infect. Dis. 155, 140 (1987), Chanock et al., J. Infect. Dis. 148, 49 (1983), Dyall-Smith et al., J. Virol. 38, 1099 (1981), Glass et al., Science 265, 1389 (1994))

VZV (*varicella zoster* virus) antigen
(Straus et al., Ann. Intern. Med. 109, 438 (1988), Gershon, Pediatr. Infect. Dis. 2, 171 (1991), Kinchington et al., J. Virol. 64, 4540 (1990))

CMV (cytomegalovirus) antigen
(Plotkin, Science 265, 1383 (1994))

Measles virus antigen
(Katz and Kellin, Science 265, 1391 (1994))

HPV (human papillomvirus) antigen
(Tindl and Frazer, Curr. Topics Microbiol. Immunol. 186, 217 (1994))

HBV (hepatitis B virus) antigen
(Valenzuela et al., Nature 280, 815 (1979), Heerman et al., J. Virol. 52, 396 (1984))

HCV (hepatitis C virus) antigen
(Cerny et al., Curr. Topics Microbiol. Immunol. 189, 169 (1994), Esteban et al., Progr. Liver Dis. 10, 253 (1992), Jung et al., Eur. J. Clin. Invest. 24, 641 (1994))

HDV (hepatitis D virus) antigen
(Iwarson, Scand. J. Infect. Dis. 24, 129 (1992), Consolo et al., Nephron. 61, 251 (1992))

HEV (hepatitis E virus) antigen
(Iwarson, Scand. J. Infect. Dis. 24, 129 (1992), Consolo et al., Nephron. 61, 251 (1992))

HAV (hepatitis A virus) antigen
(d'Hondt, Vaccine 10, 48 (1992), Andre, J. Infect. Dis. 171, 33 (1995), Lemon et al., Vaccine 10, 40 (1992), Melnick et al., Vaccine 10, 24 (1992), Flehmig, Baillieres Clin. Gastroenterol. 4, 707 (1990))

Vibrio cholera antigen
(Levine and Kaper, Vaccine 11, 207 (1993))

Borrelia burgdorferi antigen
(Schaible et al., Immunol. Letters 36, 219 (1993), Wallich et al., Lab. Med. 17, 669 (1993))

*Helicobacter pylori* antigen (Crabtree et al., Lancet 338, 332 (1991), Blaser, J. Infect. Dis. 161, 626 (1990), Cover and Blaser, J. Biol. Chem. 267, 10570 (1993), Cover et al., Infect. Immunol. 58, 603 (1990), Dunn et al., J. Biol. Chem. 265, 9464 (1990), Dunn et al., Infect. Immunol. 60, 1946 (1992), Lage et al., Acta Gastroenterol. Belg. 56 (suppl.), 61 (1993), Mobley et al., Scand. J. Gastroint. 26 (suppl. 187), 39 (1991))

Malaria antigen
(Nussenzweig and Long, Science 265, 1381 (1994), Maurice, Science 267, 320 (1995), Enders et al., Vaccines 10, 920 (1992), Knapp et al., Infect. Imm. 60, 2397 (1992))

However, within the context of the invention, active substances of this nature also include the DNA for an antiidiotype antibody or its antigen-binding fragments, whose antigen-binding structures, the complementarity determining regions, constitute copies of the protein structure or carbohydrate structure of the neutralization antigen of the infective agent.

Antiidiotype antibodies of this nature can, in particular, replace carbohydrate antigens in the case of bacterial infective agents.

Antiidiotypic antibodies of this nature, and their cleavage products, have been reviewed by Hawkins et al. (J. Immunother. 14, 273 (1993)) and Westerink and Apicella (Springer Seminars in Immunopathol. 15, 227 (1993)).

5.3 Combination of Identical or Different Active Substances for the Therapy or Prophylaxis of Infectious Diseases The invention furthermore relates to an active compound which comprises a combination of the DNA sequences of identical active substances (A,A) or of different active substances (A,B). In order to express two sequences, the cDNA of an internal ribosome entry site (IRES) is preferably intercalated as a regulatory element.

IRES of this nature have been described, for example, by Montford and Smith, TIG 11, 179 (1995), Kaufman et al., Nucl. Acids Res. 19, 4485 (1991), Morgan et al., Nucl. Acids Res. 20, 1293 (1992), Dirks et al., Gene 128, 247 (1993), Pelletier and Sonenberg, Nature 334, 320 (1988) and Sugitomo et al., BioTechn. 12, 694 (1994).

Figure 8:
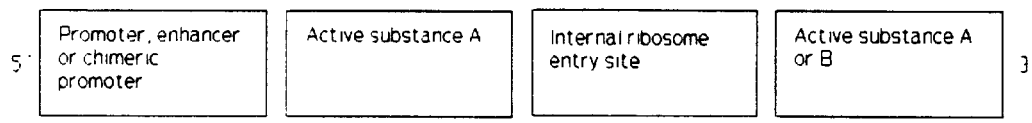
FIG. 8 depicts the arrangement of the individual components for the viral substance A and the antiviral substance B.

Thus, the cDNA of the poliovirus IRES sequence (position $\leq 140$ to $\geq 630$ of the 5' UTR (Pelletier and Sonenberg, Nature 334, 320 (1988)) can be used to link the DNA of the viral substance A (at the 3' end) and the DNA of the antiviral substance B (at the 5' terminus) (see FIG. 8).

Depending on the combination, an active compound of this nature exhibits an additive (A+A, A+B1) or synergistic effect within the context of the invention.

Thus, for the therapy of viral diseases, for example, two identical or two different antiviral active substances can be combined with each other.

In the prophylaxis of infectious diseases, several active substances, which encode different antigens of an infectious agent or of different infectious agents, can be combined with each other. Furthermore, the active substance which encodes the antigen of an infectious agent can be combined with an active substance which encodes a cytokine or a cytokine receptor.

The cytokines or cytokine receptors which are thus formed (after injection of the active compound) at the same time as the infective agent antigen can influence the nature and strength of the developing immune reaction.

DNA sequences for cytokines and cytokine receptors which amplify the humoral or cellular immune reaction have already been described under 3.1.

The following are examples of DNA sequences for cytokines which amplify the immune reaction as a whole:

Il-1α
  (Fenton, Int. J. Immunopharm. 14, 401 (1992), Furntani et al., Nucl. Acids Res. 14, 3167 (1986), Lafage et al., Blood 73, 104 (1989), March et al., Nature 315, 641 (1985))

Il-1β
  (Bensi et al., Gene 52, 95 (1987), Auron et al., PNAS 81, 7907 (1984), Clark et al., Nucl. Acids Res. 14, 7897 (1986))

Il-2
  (Fletscher et al., Lymphok. Res. 6, 45 (1987), Matsui et al., Lymphokines 12, 1 (1985), Tanaguchi et al., Nature 302, 305 (1983))

GM-CSF
  (Gough et al., Nature 309, 763 (1984), Nicola et al., J. Biol. Chem. 254, 5290 (1979), Wong et al., Science 228, 810 (1985))

6. Active Compound for Treating Tumors
6.1. Selection of the Promoters or Activator Sequences for Tumor Cells A gene-regulatory nucleotide sequence with which transcription factors interact which are formed or are active in tumor cells is designated as the promoter or activator sequence.

Those tumors are preferred which are directly available to the novel nucleic acid constructs. These tumors are, for example, leukemia cells (in addition to proliferating endothelial cells in the vicinity of solid tumors of differing type) following intravenous administration of the nucleic acid constructs, ovarian carcinomas and pancreatic carcinomas, for example, following intraperitoneal injection of the constructs, and lung carcinomas, for example, following intrabronchial administration of the constructs.

Within the context of this invention, the preferred promoters or activator sequences include gene-regulatory sequences or elements from genes which encode proteins which are formed, in particular, in leukemia cells, cancer cells or sarcoma cells. Thus, the promoter for the N-CAM protein is preferably used in the case of small-cell bronchial carcinomas, while the promoter for hepatitis growth factor receptor or for L-plastin is preferably used in the case of ovarian carcinomas, the promoter for L-plastin or for polymorphic epithelial mucin (PEM) is preferably used in the case of pancreatic carcinomas, and the promoter for prostate-specific antigen (PSA) is preferably used in the case of prostate tumors.

6.2. Selection of the Structural Genes for Active Substances for Tumor Cells Within the context of the invention, an active substance is to be understood as being a DNA sequence whose expressed protein inhibits the proliferation of cells, in particular of leukemia cells as well. These cell cycle inhibitors include, for example, the DNA sequences for inhibitory cytostatic and cytotoxic proteins, for antibodies or antibody cleavage products and for enzymes, as have already been described.

A cell cycle inhibitor is furthermore to be understood as being a DNA sequence which expresses a protein which, directly or indirectly, exhibits a cytostatic or cytotoxic effect on tumor cells or leukemia cells.

A cell cycle inhibitor is also to be understood as being the DNA sequence for a ribozyme which catalyzes the mRNA of the genes for cell cycle control proteins. An active substance for tumor cells is also to be understood as being a DNA sequence whose expressed protein or peptide constitutes a tumor antigen which triggers an immune reaction.

7. Active Compound for Inhibiting the Proliferation of Smooth Muscle Cells in Association with Blood Vessel Occlusions
7.1. Selection of the Promoters or the Activator Sequences for Smooth Muscle Cells Promoters or activator sequences composed of promoters or enhancers which are to be used within the context of the invention are preferably gene-regulatory sequences or elements from genes which encode proteins which are formed, in particular, in smooth muscle cells.

7.2. Selection of the Structural Genes for Active Substances for Smooth Muscle Cells Within the context of the invention, an active substance is to be understood as being a DNA sequence whose expressed protein inhibits the proliferation of smooth muscle cells. These proliferation inhibitors include the proteins which have already been mentioned under 1.2.a) and 1.2.c).

However, an active substance is also to be understood as being the DNA sequence for an enzyme which converts an inactive precursor of a cytostatic agent into a cytostatic agent (see 1.2.e)).

However, an active substance is also to be understood as being the DNA sequence for a ribozyme which is specific for the mRNA of genes for cell cycle control proteins like cyclin and cyclin dependent kinase.

8. Active Compound for Exerting an Effect on Coagulation 8.1. Selection of the Promoters or the Activator Sequences for Exerting an Effect on Coagulation Within the context of the invention, the promoters or activator sequences to be used are preferably gene-regulatory sequences or elements from genes which encode proteins which can be detected in smooth muscle cells, in activated endothelial cells, in activated macrophages or in activated lymphocytes. 8.1. a) Smooth Muscle Cells Examples of promoter sequences for genes in smooth muscle cells have already been given.

8.1.b) Activated Endothelial Cells

Examples of proteins which are formed in activated endothelial cells, in particular, have been described by Burrows et al. (Pharmac. Ther. 64, 155 (1994)). These proteins include, in particular, proteins which appear to an increased extent in endothelial cells, for example those proteins which, together with the promoter sequences for their genes, have already been cited above.

8.1.c) Activated Macrophages and/or Activated Lymphocytes

Within the context of this invention, activator sequences are also to be understood as being promoter sequences of the genes for proteins which are formed to an increased extent in macrophages and/or lymphocytes during the immune reaction. Proteins of this nature have already been cited.

8.2. Selection of the Structural Genes for Active Substances for Exerting an Effect on Coagulation An active substance to be used within the context of this invention is a DNA sequence which encodes a protein which, directly or indirectly, inhibits thrombocyte aggregation or a blood coagulation factor or stimulates fibrinolysis.

An active substance of this nature is termed a coagulation inhibitor. Genes for plasmin or plasminogen activators (PAs), such as tissue PA (tPA) or urokinase-like PA (uPA), or protein C, antithrombin III, C-1S inhibitor, α1-antitrypsin, tissue factor pathway inhibitor (TFPI) or hirudin, for example, are to be employed as coagulation inhibitors.

However, a DNA sequence which encodes a protein which promotes blood coagulation is also to be used as an active substance within the context of this invention. Examples of proteins of this nature are blood plasma proteins such as FVIII or FIX or tissue factor.

9. Active Compound for Protecting Against CNS Damage 9.1. Promoters or Activator Sequences Formed From Promoters or Enhancers for an Active Compound for Protecting Against CNS Damage 9.1.a) Promoters or Activator Sequences Which are Activated in Endothelial Cells These include, in particular, the promoter sequences for the genes for endothelial cell-specific proteins.

9.1.b) Promoters or Activator Sequences which are Activated in Glia Cells

A preferred activator sequence is also to be understood as being a nucleotide sequence (promoter sequence or enhancer sequence) which interacts with transcription factors which are formed, or are active, to an especial extent in glia cells.

9.2 Choice of the Structural Genes for Neurospecific Factors

Within the context of the invention, a neurospecific factor is to be understood as being a DNA sequence which encodes a neuronal growth factor.

The invention is explained in more detail with the aid of the following examples, without being restricted to these examples.

EXAMPLE 1

Preparation of a Hybrid Promoter

The novel hybrid promoter is composed of the following different nucleotide sequences, which follow each other in a downstream direction:

Element I the promoter of the VEGF receptor I gene (nucleotides −1195 to 100; Morishita et al., J. Biol. Chem. 270, 27948 (1995).The TATA box (nucleotides TATAAA in position −31 to −26) is mutated to TGTAAA)

the sequence GCCACC (Kodak, J. Cell Biol. 108, 229 (1989))

the cDNA for the immunoglobulin signal peptide (nucleotide sequence 63 to 107; Riechmann et al., Nature 332, 323 (1988))

the cDNA for β-glucuronidase (nucleotide sequence 93 to 1982; Oshima et al., PNAS USA 84, 685 (1987))

Element II the promotor of the cdc25C gene (nucleotides −487 to +121, preferably nucleotides −487 to +247; Jahroudi and Lynch, Mol. Cell Biol. 14, 999 (1994), in particular nucleotides −290 to +121)

the gene for the TATA box-binding protein (nucleotide sequence +1 to +1001, which is mutated in nucleotides 862 (A replaced with T) 889 and 890 (GT replaced with AC) and 895 (C replaced with G) (Strubin and Struhl, Cell 68, 721 (1992); Heard et al., EMBO J. 12, 3519 (1993))

Figure 9:
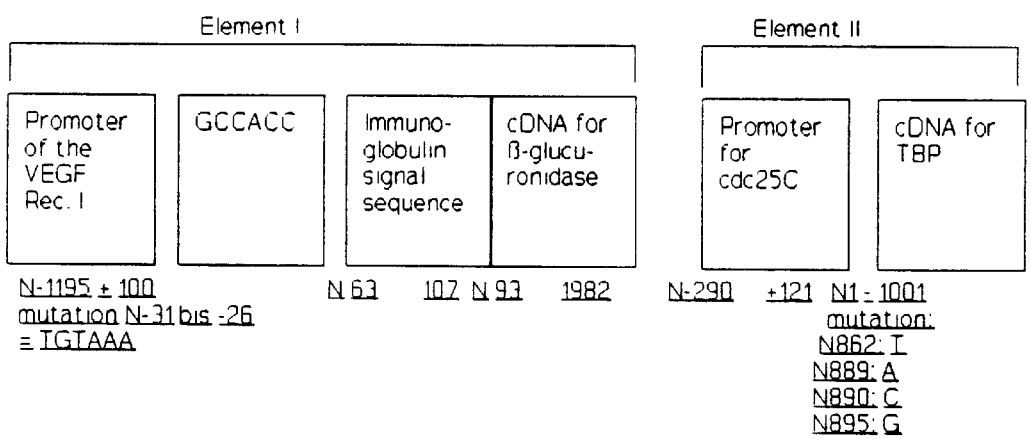
FIG. 9 depicts a hybrid promoter of the present invention containing Element I and Element II linked together.

The nucleotide sequences of Element I and Element II are linked as shown in the scheme in FIG. 9.

The nucleotide construct which has been prepared in this way is cloned into pUC 18/19 or Bluescript-derived plasmid vectors, which are then used for in vivo administration, either directly or in colloidal dispersion systems.

The individual components of the construct are linked via suitable restriction sites, which are introduced at the termini of the different elements during PCR amplification. The linking is carried out using enzymes which are specific for the restriction sites, and which are known to the skilled person, and DNA ligases.

Human umbilical cord endothelial cells and fibroblasts (Wi-38) which are being maintained in culture are transfected with one of the described plasmids using a method known to the skilled person (Lucibello et al., EMBO J. 14, 132 (1995)), and the quantity of β-glucuronidase which is produced by the endothelial cells is measured using 4-methylumbelliferyl-β-glucuronide as the substrate.

In order to check the cell cycle specificity, endothelial cells are synchronized in G0/G1 by the removal of methionine over 48 hours (Nettelbeck et al., publication in preparation). The DNA content of the cells is determined in a fluorescence-activated cell sorter after staining with Hoechst 33258 (Lucibello et al., EMBO J. 14, 132 (1995)).

The following results were obtained:

No increase in β-glucuronidase can be detected in transfected fibroblasts as compared with non-transfected fibroblasts.

Transfected endothelial cells express substantially more β-glucuronidase than do non-transfected endothelial cells.

Proliferating endothelial cells (DNA >2 S; S=single chromosomal set) secrete substantially more β-glucuronidase than do endothelial cells which are synchronized in G0/G1 (DNA=2 S).

The multiple promoter unit which has been described therefore gives rise to cell-specific, cell cycle-dependent expression of the β-glucuronidase structural gene.

EXAMPLE 2

Preparation of a Hybrid Promoter in Combination with a Nuclear Retention Signal (NRS) and a Nuclear Export Factor (NEF)

The novel hybrid promoter is composed of the following different nucleotide sequences, which follow each other in a downstream direction:

Element III
  the promoter of the VEGF receptor I gene
  (nucleotides −1195 to 100; Morishita et al., J. Biol. Chem. 270, 27948 (1995). The TATA box (nucleotides TATAAA in position −31 to −26) is mutated to TGTAAA)
  the sequence GCCACC
  (Kodak, J. Cell Biol. 108, 229 (1989))
  the cDNA for the immunoglobulin signal peptide
  (nucleotide sequence 63 to 107; Riechmann et al., Nature 332, 323 (1988))
  the cDNA for β-glucuronidase
  (nucleotide sequence 93 to 1982; Oshima et al., PNAS USA 84, 685 (1987))
  the cDNA for the HIV-1 virus RRE as the nuclear retention signal (NRS)
  (nucleotide sequence 7357 to 7602; Ratner et al., Nature 313, 277 (1985); Malim et al., Nature 338, 254 (1989)).
Element IIa
  the promoter of the cdc25C gene
  (nucleotides −290 to +121; Zwicker et al., EMBO J. 14, 4514 (1995); Zwicker et al. Nucl. Acids Res. 23, 3822 (1995))
  the gene for the TATA box-binding protein containing comutations
  (nucleotide sequence 1–1001 which is mutated at nucleotides 862 (A replaced with T) 889 and 890 (GT replaced with AC) and 895 (C replaced with G) (Strubin and Struhl Cell 68, 721 (1992); Heard et al. EMBO J. 12, 3519 (1993)).
Element IV
  the promoter of the von Willebrand factor (vWF) gene
  (nucleotides −487 to +247; Jahroudi and Lynch, Mol Cell Biol. 14, 999 (1994))
  the cDNA for the HIV-1 virus REV as the nuclear export factor (NEF) amino acid sequence 1–117; Ratner et al., Nature 313, 277 (1985).

Figure 10:
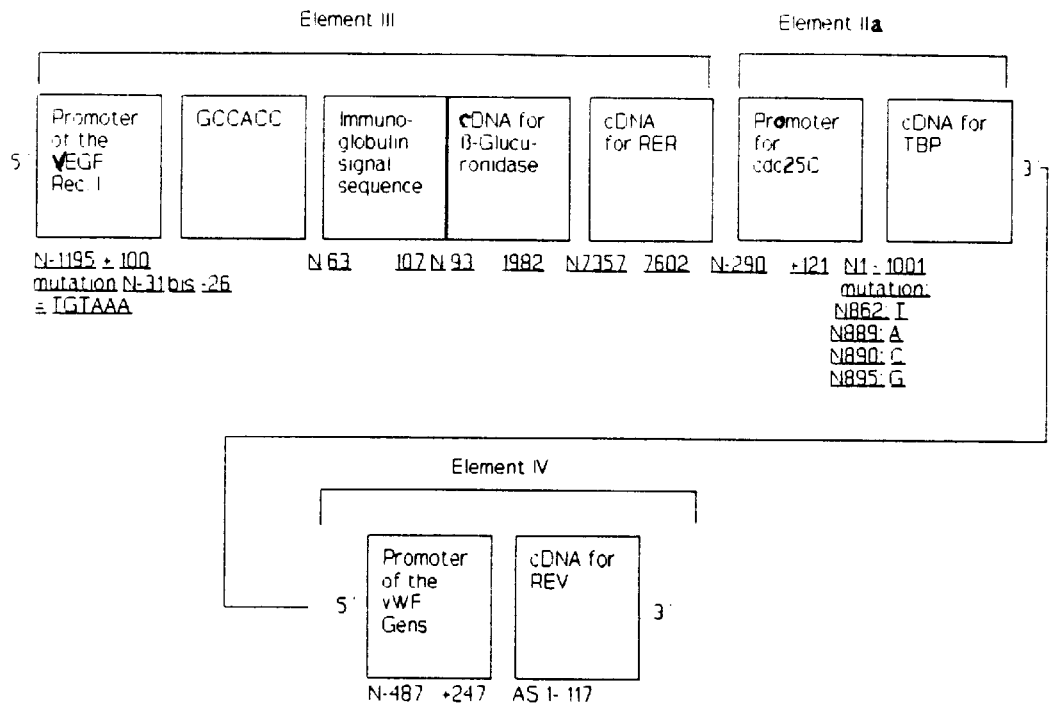
FIG. 10 depicts a hybrid promoter of the present invention containing Elements IIa, III and IV linked together.

The nucleotide sequences of elements IIa, III and IV are linked as shown in the scheme in FIG. 10.

The nucleotide construct which has been prepared in this way is cloned into pUC18/19 or Bluescript-derived plasmid vectors, which are used for in-vivo administration either directly or in colloidal dispersion systems.

The individual components of the construct are linked via suitable restriction sites, which are introduced at the termini of the different elements during PCR amplification. The linking is effected using enzymes which are specific for the restriction sites, and which are known to the skilled person, and DNA ligases.

Human umbilical cord endothelial cells and fibroblasts (Wi-38) which are being maintained in culture are transfected with the described plasmid using a method known to the skilled person (Lucibello et al., EMBO J. 14, 132 (1995)), and the quantity of β-glucuronidase which is produced by the endothelial cells is measured using 4-methylumbelliferyl-β-glucuronide as the substrate.

In order to check the cell cycle specificity, endothelial cells are synchronized in G0/G1 by the removal of methionine over 48 hours (Nettelbeck et al., publication in preparation). The DNA content of the cells is determined in a fluorescence-activated cell sorter after staining with Hoechst 33258 (Lucibello et al., EMBO J. 14, 132 (1995)).

The following results are obtained:

It is not possible to detect any increase in β-glucuronidase in transfected fibroblasts as compared with non-transfected fibroblasts.

Transfected endothelial cells express substantially more β-glucuronidase than do non-transfected endothelial cells.

Proliferating endothelial cells (DNA >2 S) secrete substantially more β-glucuronidase than do endothelial cells which are synchronized in G0/G1 (DNA=2 S).

The multiple promoter unit which has been described therefore gives rise to cell-specific, cell cycle-dependent expression of the β-glucuronidase structural gene.

EXAMPLE 3

Preparation of a Hybrid Promoter in Combination with an Activator-responsive Promoter Unit The novel activator-responsive promoter unit is composed of the following different nucleotide sequences, which follow each other in a downstream direction:

Element V
  Activator Subunit A
  the promoter of the cdc25C gene
  (nucleotides −290 to +121; Zwicker et al., EMBO J. 14, 4514 (1995); Zwicker et al., Nucl. Acids Res. 23, 3822 (1995))
  the cDNA for the DNA-binding domain of the Gal4 protein
  (amino acids 1 to 147; Chasman and Kornberg, Mol. Cell Biol. 10, 2916 (1990))
  the cDNA for Gal80
  (amino acids 1 to 435; Leuther et al., Science 256, 1333 (1992))
  Activator Subunit B
  the promoter of the VEGF receptor I gene
  (nucleotides −1195 to +100; Morishita et al., J. Biol. Chem. 270, 27948 (1995) with the TGTAAA mutation in nucleotides −31 to −26)
  the cDNA for the Gal80-binding domain of Gal14
  (amino acids 851 to 881; Leuther et al., Science 256, 1333 (1992))
  the nuclear localization signal (NLS) of SV40
  (SV40 large T; amino acids 126 to 132: PKKKRKV SEQ ID NO. 1); Dingwall et al., TIBS 16, 478 (1991))
  the acid transactivating domain (TAD) of HSV-1 VP16
  (amino acids 406 to 488; Triezenberg et al., Genes Developm. 2, 718 (1988); Triezenberg, Curr. Opin. Gen. Developm. 5, 190 (1995))
  Activator-responsive Promoter
  the binding sequence for Gal4 having the nucleotide sequence 5'-CGGACAACTGTTGAC CG-3' (SEQ ID NO.: 2, Chasman and Kornberg, Mol. Cell Biol. 10, 2916 (1999)) coupled to the SV40 basal promoter (nucleotides 48 to 5191; Tooze (ed.), DNA Tumor Viruses (Cold Spring Harbor New York, N.Y.; Cold Spring Harbor Laboratory).

Figure 11:
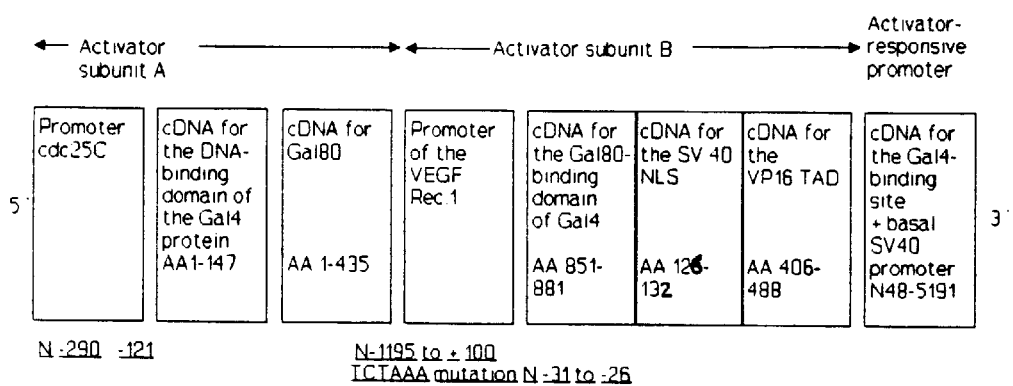
FIG. 11 depicts the nucleotide sequences of one of the preferred activator-responsive promoter units of the present invention.

The order of the nucleotide sequences of the activator-responsive promoter units is shown by the scheme in FIG. 11.

The described activator sequence functions as follows:

The cdc25C promoter regulates transcription of the combined cDNA's for the Gal4 binding protein and for Gal80 in a cell cycle-specific manner.

The VEGF receptor I promoter restricts transcription of the coupled cDNA for the Gal80-binding domain of Gal4, the SV40 NSL and the TAP to endothelial cells. However, its activation is inhibited by the mutation.

The expression products of activator subunits A and B dimerize by the binding of the Gal80-binding domain of Gal4 to Gal80.

Figure 12:
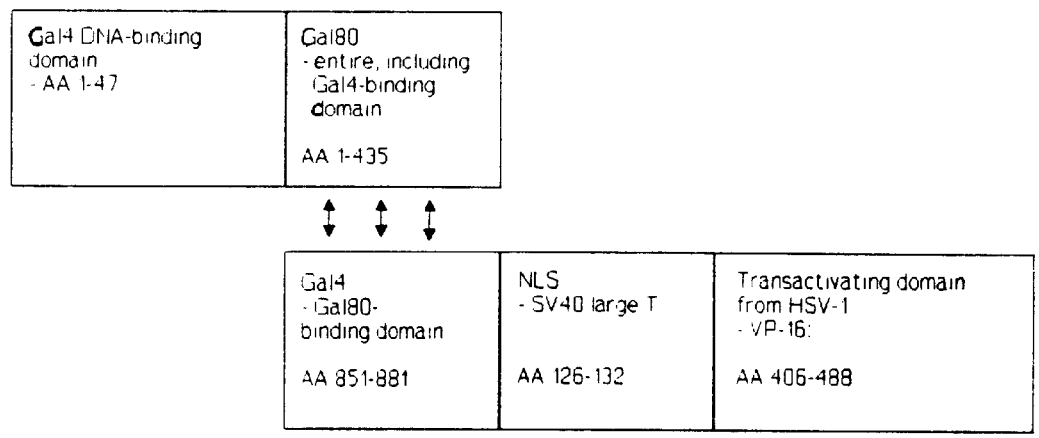
FIG. 12 depicts the fusion protein of activator subunit A (upper 2 rectangles) that dimerizes with the fusion protein of the activator subunit B (lower three rectangles) by the binding of the Gal80-binding domain of Gal4 to Gal80 (vertical double-headed arrows).

The dimerization is shown diagrammatically in FIG. 12.

The dimeric protein is a chimeric transcription factor for the activator-responsive promoter DNA sequence for the Gal4 binding domain/SV40 promoter.

Figure 13:
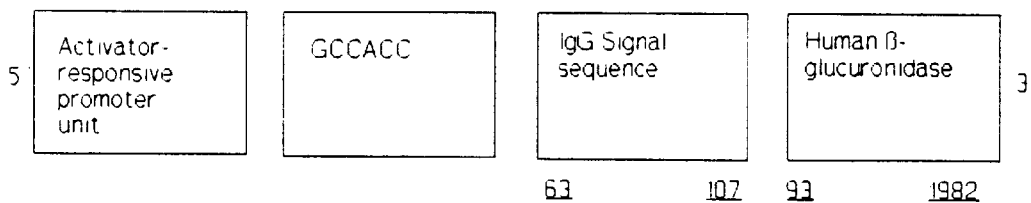

The promoter is now linked, at its 3' end, to the sequence GCCACC (Kocak, J. Cell Biol. 108, 229 (1989)), and the latter is linked to the cDNA for the immunoglobulin signal peptide (nucleotide sequence 63 to 107; Riechmann et al., Nature 332, 323 (1988)). This is followed by the cDNA for β-glucuronidase (nucleotide sequence 93 to 1982; Oshima et al., PNAS USA 84, 685 (1987)) in accordance with the scheme in FIG. 13.

This unit is, in turn, connected, at its 3' end, to the element VI, which element VI can, however, also be added onto the 5' end of the nucleotide construct.

Element VI

Element VI Comprises:

the promoter of the von Willebrand factor gene (nucleotides −487 to +247; Jahroudi and Lynch, Mol. Cell. Biol. 14, 999 (1994))

the gene for the TATA-box binding protein (nucleotide sequence 1–1001) which is mutated in nucleotides 862 (A replaced with T); 889 and 890 (GT replaced with AC) and 895 (C replaced with G).

The comutation in the TATA box-binding protein relieves the inhibition of the activation of the VEGF receptor promoter (activator subunit B).

The nucleotide construct which has been prepared in this way is cloned into pUC 18/19 or Bluescript-derived plasmid vectors, which are used for in-vivo administration either directly or in colloidal dispersion systems.

The individual components of the construct are linked by way of suitable restriction sites which are incorporated at.the termini of the different elements during PCR amplification. The linking is effected using enzymes which are specific for the restriction sites and which are known to the skilled person, and DNA ligases.

Human umbilical cord endothelial cells and fibroblasts (Wi-38) which are being maintained in culture are transfected with the described plasmid using a method known to the skilled person (Lucibello et al., EMBO J. 14, 132 (1995)), and the quantity of β-glucuronidase which is produced by the endothelial cells is measured using 4-methylumbelliferyl-β-glucuronide as a substrate.

In order to check the cell cycle specificity, endothelial cells are synchronized in G0/G1 by the removal of methionine over 48 hours (Nettelbeck et al., publication in preparation). The DNA content of the cells is determined in a fluorescence-activated cell sorter after staining with Hoechst 33258 (Lucibello et al., EMBO J. 14, 132 (1995)).

The following results are obtained:

It is not possible to detect any increase in β-glucuronidase in transfected fibroblasts as compared with non-transfected fibroblasts.

Transfected endothelial cells express substantially more β-glucuronidase than do non-transfected endothelial cells.

Proliferating endothelial cells (DNA >2 S) secrete substantially more β-glucuronidase than do endothelial cells which are synchronized in G0/G1 (DNA=2 S).

The multiple promoter unit which has been described therefore gives rise to cell-specific, cell cycle-dependent expression of the β-glucuronidase structural gene.

An active compound according to the present invention, as described in Examples I–III, has the effect of ensuring, following local administration, for example at the site of the tumor, or following intracranial or subarachnoid administration, or systemic, preferably intravenous or intraarterial administration, that, as a result of the cell cycle specificity or endothelial cell specificity of the activator-responsive promoter unit, it is mainly, if not exclusively, only proliferating endothelial cells which secrete β-glucuronidase. This β-glucuronidase cleaves a well tolerated doxorubicin-β-glucuronide (Jacquesy et al., EPO 0 511 917 A1), which is now injected, into doxorubicin, which has a cytostatic effect. The doxorubicin inhibits endothelial cell proliferation and exerts a cytostatic effect on these cells and on neighboring tumor cells. This results in tumor growth being inhibited.

The specification, claims, drawings, and abstract of the Federal Republic of Germany Application No. 19639103.2 filed on Sep. 24, 1996 is herein incorporated in its entirety by reference. Additionally, all of the citations to which reference was made in the specification are herein incorporated in their entirety by reference.

We claim:

1. A nucleic acid construct for the regulated expression of a transgene in a host cell comprising in a 5' to 3' end direction reading frame, the following components:
   (i) a first promoter or enhancer sequence (a), which activates the transcription of said transgene or a first promoter or enhancer sequence (a') which contains a mutation which inhibits the function of the first promoter (a');
   (ii) a transgene (b') encoding a pharmacologically active compound or a transgene (b) containing
      (1) a nuclear retention signal (NRS) which is linked, at its 5' end to the 3' end of the transgene, wherein the transcription product of the NRS provides a structure for binding a nuclear export factor (NEF), and
      (2) a mutation which inhibits the transcription and/or the translation of said transgene or inhibits the function of the pharmacologically active compound encoded by said transgene;
   (iii) a second promoter or enhancer sequence (c), which activates the basal transcription of the component (d) or which contains a mutation which inhibits the function of the second promoter; and
   (iv) a gene (d) encoding a tRNA or a regulatory protein for abolishing the mutation in at least one of the promoters (a) and (c) or in the transgene (b).

2. The nucleic acid construct of claim 1, further comprising the following components:
   (v) a third promoter or enhancer sequence (i) which activates the basal transcription of the NEF, and
   (vi) a nucleic acid sequence (k), encoding the NEF, which binds to the transcription product of NRS, thereby mediating transport of the transcription product of the transgene out of the cell nucleus into the cytoplasm.

3. The nucleic acid construct of claim 2, wherein at least one of the promoter or enhancer sequences (a), (c), and (i) is an activator-responsive promoter unit which comprises the following components:
   (vii) at least one promoter or enhancer sequence (e), which can be activated by at least one activation method selected from the group consisting of nonspecifically, virus-specifically, metabolically, cell-specifically and cell cycle-specifically;
   (viii) at least one nucleic acid encoding an activator subunit (f) which is situated downstream from the promoter or enhancer sequence (e), and wherein the basal transcription of the activator subunit is activated by the promoter or enhancer sequence (e); and
   (ix) an activator-responsive promoter (g) which is activated by the expression products of the activator subunit (f), or of several identical (f) subunits, or by different (f') activator subunits located downstream of promoter or enhancer sequences (e'), wherein the basal transcription of the activator subunit is activated by the promoter or enhancer sequence (e').

4. The nucleic acid construct of claim 2, wherein the nucleic acid sequence encoding the NRS is selected from the group consisting of the Rev-responsive element (RRE) from HIV-1 or HIV-2, the RRE-equivalent retention signal from retroviruses other than HIV-1 and HIV-2, and the RRE-equivalent retention signal from HBV.

5. The nucleic acid construct of claim 2, wherein the NEF (k) is selected from the group consisting of the rev gene from retrovirus, the gene encoding the hnRNP-A1 protein and the gene encoding the transcription factor TFIII-A.

6. The nucleic acid construct of claim 3, in which at least one of the promoter or enhancer sequences (a), (c) or (i), and the activator-responsive promoter (g) is a chimeric promoter, and the activator subunit (f) is a gene encoding at least one transcription factor which activates the chimeric promoter.

7. The nucleic acid construct of claim 3, wherein the activator-responsive promoter (g) is monomers or multimers of the LexA operator in combination with the SV40 promoter and is activated by two activator-subunits (f) and (f'); wherein
   the activator subunit (f) comprises a cDNA encoding the LexA DNA-binding protein whose 3' end is linked to the 5' end of a cDNA encoding the Gal80 protein; and
   the activator subunit (f') comprises in a 5' to 3' end reading frame, a cDNA encoding the Gal80-binding domain of the Gal4 protein, a cDNA encoding the SV40 large T antigen, and a cDNA encoding the transactivating domain of HSV-1 VP16.

8. The nucleic acid construct of claim 3, wherein the activator-responsive promoter (g) is monomers or multimers encoding the binding sequence for the Gal4 binding protein and the activator subunit (f) contains a nuclear localization signal (NLS) from SV40 large T antigen, and the acid transactivating domain (TAD) from HSV-1 VP16, or the activator subunit (f') contains the nuclear localization signal (NLS) from SV40 large T, a cDNA encoding the DNA-binding domain of the Gal4 protein, and a cDNA encoding the CD4-binding sequence of the p56 lck protein.

9. The nucleic acid construct of claim 3, wherein at least one TATA sequence in at least one of the promoters (a), (c), (g), and (i) is mutated and component (d) is a gene encoding a TATA-binding protein (TBP) which is mutated and binds to the mutated TATA box, enabling transcription.

10. The nucleic acid construct of claim 5, wherein the retrovirus is selected from the group consisting of HIV-1, HIV-2, visna-maedi-virus, caprine arthritis encephalitis virus, equine infectious anemia virus, feline immunodeficiency virus and HTLV.

11. The nucleic acid construct of claim 7, wherein the cDNA encoding the LexA DNA-binding protein encodes amino acids 1–81 or 1–202 of the LexA DNA-binding protein, the cDNA encoding the Gal80 protein encodes amino acids 14–35 of the Gal80 protein, the CDNA encoding the Gal80-binding domain of the Gal4 protein encodes amino acids 851–881 of the Gal4 protein, the cDNA encoding the SV40 large T antigen encodes amino acids 126–132 of the SV40 large T antigen, and the CDNA encoding the transactivating domain encodes amino acids 406–488 of HSV-1 VP16.

12. The nucleic acid construct of claim 7, wherein the monomers or multimers of the LexA operator are replaced with monomers or multimers of the Gal4 binding region and the cDNA encoding the LexA DNA-binding protein is replaced with a cDNA encoding the DNA-binding domain of the Gal4 protein.

13. The nucleic acid construct of claim 8, wherein NLS encodes SEQ ID NO.: 1, and the TAD encodes amino acids 406–488 from HSV-1 VP16, the cDNA for the DNA-binding domain of the Gal4 protein encodes amino acids 1–147 of the Gal4 protein, and the cDNA for the CD4-binding sequence encodes amino acids 1–71 of the p56 Ick protein.

14. The nucleic acid construct of claim 9, wherein the TATA box is mutated to TGTAAA and the gene encoding the TBP is mutated to T in N862, to A in N889, to C in N890 and to G in N895.

15. The nucleic acid construct of claim 14, comprising a hybrid promoter containing in a 5' to 3' end direction reading frame, the following elements:
Element I comprising:
the promoter of the VEGF receptor I gene containing nucleotides −1195 to +100, wherein the nucleotides of the TATA box of TATAAA in position −31 to −26 are mutated to TGTAAA;
the sequence GCCACC;
nucleotide sequence 63 to 107 of the cDNA encoding the immunoglobulin signal peptide; and
nucleotide sequence 93 to 1982 of the cDNA encoding β-glucuronidase; and
Element II comprising:
nucleotides −487 to +121 of the promoter of the cdc25C gene;
nucleotide sequence +1 to +1001 of the TATA box-binding protein, which is mutated in nucleotides 862 (A replaced with T), 889 and 890 (GT replaced with AC) and 895 (C replaced with G).

16. The nucleic acid construct of claim 14, comprising a hybrid promoter containing in a 5' to 3' direction reading frame, the following elements:
Element III
the promoter of the VEGF receptor I gene containing nucleotides −1195 to 100, and wherein the nucleotides of the TATA box of TATAAA in position −31 to −26 are mutated to TGTAAA;
the sequence GCCACC;
nucleotide sequence 63 to 107 of the cDNA encoding the immunoglobulin signal peptide; and
nucleotide sequence 93 to 1982 of the cDNA encoding -glucuronidase; and
nucleotide sequence 7357 to 7602 of a cDNA encoding HIV-1 RRE as the nuclear retention signal (NRS); and
Element IIa
nucleotides −290 to +121 of the promoter of the cdc25C gene; and
nucleotide sequence +1 to +1001 of the TATA box -binding protein, which is mutated in nucleotides 862 (A replaced with T), 889 and 890 (GT replaced with AC) and 895 (C replaced with G); and
Element IV
nucleotides −487 to +247 of the promoter of the von Willebrand factor (vWF) gene; and
a cDNA for HIV-1 virus REV encoding amino acid sequences 1–117 as the nuclear export factor (NEF).

17. The nucleic acid construct of claim 14, comprising a hybrid promoter and an activator-responsive promoter unit containing in a 5' to 3' end direction reading frame, which contains the following elements:
Element V comprising:
1) Activator subunit A comprising:
nucleotides −290 to +121 of the promoter of the cdc25C gene;
a cDNA for the DNA-binding domain of amino acids 1 to 147 of Gal4 protein; and
a cDNA encoding amino acids 1 to 435 of Gal80;
2) Activator subunit B comprising:
the promoter of the VEGF receptor I gene containing nucleotides −1195 to +100 with TGTAAA in −31 to −26 nucleotides;
a cDNA for the Gal80-binding domain of amino acids 851 to 881 of Gal4;
a nucleic acid encoding the nuclear localization signal (NLS) comprising SEQ ID NO.: 1; and
a nucleic acid encoding an acid transactivating domain (TAD) comprising amino acids 406 to 488 of HSV-1 VP 16; and
3) Activator-responsive promoter comprising:
a binding sequence for Gal4 having the nucleotide sequence SEQ ID NO.: 2 operably linked to nucleotides 48 to 5191 of the SV40 basal promoter;
the sequence GCCACC;
nucleotide sequence 63 to 107 of the cDNA encoding the immunoglobulin signal peptide; and
nucleotide sequence 93 to 1982 of the cDNA for β-glucuronidase; and
Element VI comprising:
nucleotides −487 to +247 of the promoter of the von Willebrand factor gene; and
a gene for the TATA box-binding protein (nucleotide sequence 1–1001), which is mutated in nucleotides 862 (A replaced with T); 889 and 890 (GT replaced with AC) and 895 (C replaced with G).

* * * * *

SEQUENCE LISTING

<160> NUMBER OF SEQ ID NOS: 2

<210> SEQ ID NO 1
<211> LENGTH: 7
<212> TYPE: PRT
<213> ORGANISM: Artificial/Unknown
<220> FEATURE:
<221> NAME/KEY: misc_feature
<222> LOCATION: ()..()
<223> OTHER INFORMATION: Nuclear localization signal of SV40

<400> SEQUENCE: 1

Pro Lys Lys Lys Arg Lys Val
1               5

```
<210> SEQ ID NO 2
<211> LENGTH: 17
<212> TYPE: DNA
<213> ORGANISM: Artificial/Unknown
<220> FEATURE:
<221> NAME/KEY: misc_feature
<222> LOCATION: ()..()
<223> OTHER INFORMATION: Binding sequence for Gal4

<400> SEQUENCE: 2
cggacaactg ttgaccg                                              17
```